(12) United States Patent
Hunt

(10) Patent No.: US 7,758,873 B2
(45) Date of Patent: Jul. 20, 2010

(54) POLYSACCHARIDE CONTAINING BOTULINUM TOXIN PHARMACEUTICAL COMPOSITIONS AND USES THEREOF

(75) Inventor: Terrence J. Hunt, Corona, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/303,000

(22) Filed: Dec. 13, 2005

(65) Prior Publication Data

US 2006/0099227 A1    May 11, 2006

Related U.S. Application Data

(63) Continuation of application No. 10/359,828, filed on Feb. 7, 2003, which is a continuation-in-part of application No. 10/288,738, filed on Nov. 5, 2002, now abandoned, which is a continuation-in-part of application No. 10/047,058, filed on Jan. 14, 2002, now abandoned, which is a continuation-in-part of application No. 09/500,147, filed on Feb. 8, 2000, now abandoned.

(51) Int. Cl.
| | |
|---|---|
| A61K 39/08 | (2006.01) |
| A61K 39/02 | (2006.01) |
| A61K 39/38 | (2006.01) |
| A61K 8/02 | (2006.01) |
| A61K 38/00 | (2006.01) |

(52) U.S. Cl. ............ 424/247.1; 424/236.1; 424/234.1; 424/184.1; 424/401; 530/300; 530/324

(58) Field of Classification Search ............. 424/234.1, 424/236.1, 247.1; 530/300, 324
See application file for complete search history.

(56) References Cited

U.S. PATENT DOCUMENTS

| | | | |
|---|---|---|---|
| 3,269,912 A | 8/1966 | Grafe | |
| 3,758,382 A | 9/1973 | Knorpp | |
| 4,016,354 A | 4/1977 | Greenwood | |
| 4,029,765 A | 6/1977 | Helting | |
| 4,391,801 A | 7/1983 | Ng et al. | |
| 4,457,916 A * | 7/1984 | Hayashi et al. ............ | 424/85.2 |
| 4,578,270 A | 3/1986 | Csizer et al. | |
| 4,597,966 A | 7/1986 | Zolton et al. | |
| 4,613,500 A | 9/1986 | Suzuki et al. | |
| 4,714,611 A | 12/1987 | Yasaburgo et al. | |
| 4,904,467 A | 2/1990 | Schwulera | |
| 4,962,091 A | 10/1990 | Eppstein et al. | |
| 4,985,242 A | 1/1991 | Sekine et al. | |
| 5,118,794 A | 6/1992 | Grangeorge et al. | |
| 5,182,109 A | 1/1993 | Tamura et al. | |
| 5,401,243 A | 3/1995 | Borodic | |
| 5,437,291 A | 8/1995 | Pasricha et al. | |
| 5,445,817 A | 8/1995 | Schneerson et al. | |
| 5,466,672 A | 11/1995 | Kushnaryov et al. | |
| 5,512,547 A | 4/1996 | Johnson et al. | |
| 5,562,907 A | 10/1996 | Arnon | |
| 5,609,871 A | 3/1997 | Michael et al. | |
| 5,618,676 A | 4/1997 | Hitzeman et al. | |
| 5,670,484 A | 9/1997 | Binder | |
| 5,674,205 A | 10/1997 | Pasricha et al. | |
| 5,695,956 A | 12/1997 | McClane et al. | |
| 5,696,077 A | 12/1997 | Johnson et al. | |
| 5,698,536 A | 12/1997 | Segall et al. | |
| 5,704,297 A | 1/1998 | Hussain et al. | |
| 5,714,468 A | 2/1998 | Binder | |
| 5,721,215 A | 2/1998 | Aoki et al. | |
| 5,723,281 A | 3/1998 | Segall et al. | |
| 5,730,969 A | 3/1998 | Hora et al. | |
| 5,756,468 A | 5/1998 | Johnson et al. | |
| 5,766,605 A | 6/1998 | Sanders et al. | |
| 5,837,265 A | 11/1998 | Montal et al. | |
| 5,846,929 A | 12/1998 | Johnson et al. | |
| 5,905,143 A | 5/1999 | Johnson et al. | |
| 5,908,825 A | 6/1999 | Fasano et al. | |
| 5,919,463 A | 7/1999 | Thomas, Jr. et al. | |
| 5,919,665 A | 7/1999 | Williams | |
| 5,942,242 A | 8/1999 | Mizushima et al. | |
| 5,945,098 A * | 8/1999 | Sarno et al. ................ | 424/85.5 |
| 5,997,856 A | 12/1999 | Hora et al. | |
| 6,034,221 A | 3/2000 | Berezenko et al. | |
| 6,051,239 A | 4/2000 | Simpson et al. | |
| 6,087,327 A | 7/2000 | Pearce et al. ................... | 514/2 |

(Continued)

FOREIGN PATENT DOCUMENTS

| | | |
|---|---|---|
| CN | 1215084 | 4/1999 |
| EP | 0123291 A2 | 10/1984 |
| EP | 0150067 | 7/1985 |
| EP | 0330451 A2 | 8/1989 |
| EP | 0361991 A2 | 4/1990 |

(Continued)

OTHER PUBLICATIONS

Khawaja et al (International Journal of Dermatology, 40, May 2001, p. 311-317).*
Hankins et al (Dermatol Surg, 1998:24:181-1183).*
Hankins et al (Dermatol Surg, 1998:24:181-1183) view of Hankins et al (Dermatol Surg, 1998:24:181-1183).*
Biesman et al (Ophthalmology Times Apr. 1, 1997, 13-15).*
Khawaja et al (International Journal of Dermatology 2001, 40:311-317).*
Botox Product Information Sheet., http://www.botoxcosmetic.com/resources/pi.aspx., Accessed on Jul. 5, 2007.*

(Continued)

*Primary Examiner*—Vanessa L. Ford
(74) *Attorney, Agent, or Firm*—Claude L. Nassif; Kenton Abel; Debra Condino

(57) ABSTRACT

This invention relates to the use of a composition comprising a polysaccharide and a botulinum toxin for reducing a skin wrinkle. In some embodiments, the polysaccharide comprises disaccharides. In some embodiments, the average molecular weight of a disaccharide unit of the polysaccharide is between about 345 D and about 1,000 D.

18 Claims, No Drawings

U.S. PATENT DOCUMENTS

| | | | |
|---|---|---|---|
| 6,113,915 | A | 9/2000 | Aoki et al. |
| 6,139,845 | A | 10/2000 | Donovan |
| 6,150,133 | A | 11/2000 | Mead et al. |
| 6,238,664 | B1 | 5/2001 | Hellerbrand et al. |
| 6,346,519 | B1 | 2/2002 | Petrus |
| 6,358,917 | B1 * | 3/2002 | Carruthers et al. ............. 514/2 |
| 6,787,517 | B1 * | 9/2004 | Gil et al. ........................ 514/1 |
| 6,992,172 | B1 | 1/2006 | Chang et al. |
| 7,211,261 | B1 | 5/2007 | Moyer et al. |
| 2002/0064536 | A1 | 5/2002 | Hunt ....................... 424/236.1 |
| 2003/0118598 | A1 | 6/2003 | Hunt ....................... 424/236.1 |
| 2003/0138437 | A1 | 7/2003 | Hunt ....................... 424/236.1 |
| 2005/0244358 | A1 | 11/2005 | Ochoa ..................... 424/70.13 |

FOREIGN PATENT DOCUMENTS

| | | |
|---|---|---|
| EP | 0361991 B1 | 12/1999 |
| EP | 1273593 | 5/2002 |
| WO | WO 90/03784 | 4/1990 |
| WO | WO 96/03978 | 2/1996 |
| WO | WO 96/11699 | 4/1996 |
| WO | WO 96/37515 | 11/1996 |
| WO | WO 97/35604 * | 10/1997 |
| WO | WO 00/15245 A2 | 3/2000 |
| WO | WO 00/15245 A3 | 3/2000 |
| WO | WO 01/54711 | 1/2001 |
| WO | WO 01/26736 | 4/2001 |

OTHER PUBLICATIONS

Hankins et al (Dermatol Surg, 1998:241181-1183).*
Biesman (Opthalmology Times Apr. 1, 1997, 13-15).*
Hankins et al (Dermatol Surg, 1998:24:181-1183).*
Biesman et al (Ophthalmology Times Apr. 1, 1997, 13-15).*
U.S. Appl. No. 09/500,147, Hunt.
Arnon, S.S., *Clinical Botulism*, chapter 13, pp. 145-150 of Brin M.F. et al, editors, Scientific and therapeutic aspects of botulinum Toxin, Lippincott, Williams & Wilkins (2002).
Binz T. et al., *The Complete Sequence of Botulinum Neurotoxin Type A and Comparison with Other Clostridial Neurotoxins*, J Biological Chemistry 265(16);9153-9158:1990.
Carpenter, J.F. et al., Interactions of Stabilizing Additives with Proteins During Freeze-Thawing and Freeze-Drying and Formulation, *International Symposium on Biological Product Freeze-Drying and Formulation*, Oct. 24-26, 1990, S. Karger AG (1992), pp. 225-239.
Goodnough, M.C., et al., Stabilization of Botulinum Toxin Type A during Lyophilization, *Appl. Environ. Microbiol.*, Oct. 1992, vol. 58, No. 10, pp. 3426-3428.
Jurecka W., et al., *Hydroxyethylstarch deposits in human skin—a model for pruitus?*, Arch Dermatol Res. 1993;285(1-2):13-9.
Kohl, A., et al., *Comparison of the effect of botulinum toxin A (Botox®) with the highly-purified neurotoxin (NT201) in the extensor digitorum brevis muscle test*, Mov. Disord 2000, 15(Suppl 3):165.
Kondo H., et al, *Titration of botulinum toxins for lethal toxicity by intravenous injection into mice*, Jpn J Med Sci Biol 1984;37:131-5.
Parth E., et al., *Histological and immunohistochemical investigations of hydroxyethyl-starch deposits in rat tissues*, Eur Surg Res. 1992;24(1):13-21.
Reimann S., et al., [*Hydroxyethyl starch accumulation in the skin with special reference to hydroxyethyl starch-associated pruitus*]; Dtsch Med Wochenschr. Mar. 10, 2000; 125(10):280-5.
Schantz E.J., et al Preparation and characterization of botulinum toxin type A for human treatment, chapter 3 of Eds. Jankovic, J., et al, *Therapy with Botulinum Toxin*, Marcel Dekker, Inc (1994).
Schantz, E.J., et al, *Properties and use of Botulinum toxin and Other Microbial Neurotoxins in Medicine*, Microbiol Rev. 56 (1992), pp. 80-99.
Schmidt, J.J. et al., Endoproteinase Activity of Type A Botulinum Toxin in Medical Research: Substrate Requirements and Actiation by Serum Albumin, *Journal of Protein Chemistry*, 1997, vol. 16, No. 1, pp. 19-26.
Singh, B.R., Critical Aspects of Bacterial Protein Toxins, *Natural Toxins II*, 1996, Plenum Press, New York, pp. 63-84.
Sirtl, C., *Tissue deposits of hydroxyethyl starch (HES): dose-dependent and time-related*, Br J Anaesth. Apr. 1999;82(4):510-5.
Anderson and Harvey, *Masticatory Muscle Myositis*, Journal of Veterinary Dentistry, 1993; 10(1):6-8.
Annese, V., et al., *Comparison of Two Different Formulations of Botulinum Toxin A for the Treatment of Oesophageal Achalasia*, Alimentary Pharmacology & Therapeutics, 1999; 13:1347-1350.
Aoki, K.R., *Pharmacology and Immunology of Botulinum Toxin Serotypes*, Journal of Neurology, 2001; 248(Suppl 1):Jan. 3-Jan. 10.
Aoki, R., *Preclinical update on BOTOX® (botulinum toxin type-A)-purified neurotoxin complex relative to other botulinum neurotoxin preparations*, European Journal of Neurology, 1999; 6(Suppl 4):S3-S10.
Ballance, et al., *Yeast-derived recombinant human albumin (Recombumin)*, Anasthesiol Intensivmed Notfallmd Schmerzther, 1999; 34(12):775-777.
Banga, *Therapeutic Peptides and Proteins: Formulation, Processing and Delivery Systems*, $2^{nd}$ Edition, CRC Press, Boca Raton, FL, pp. 108-110, 1995.
Begg, G.E. and David W. Speicher, *Mass Spectrometry Detection and Reduction of Disulfide Adducts Between Reducing Agents and Recombinant Proteins With Highly Reactive Cysteines*, Journal of Biomolecular Techniques, 1999; 10(1):17-20.
Bigalke, H., et al., *Blockade by Tetanus and Botulinum A Toxin of Postganglionic Cholinergic Nerve Endings in the Myenteric Plexus*, Nauyn-Schmiedeberg's Archives of Pharmacology 312, 255-263 (1980).
Bigalke, H., et al., *Factors Influencing Potency of Botulinum Toxin in Man*, Society for Neuroscience, 1997; 23(870.10):2234.
BioTime, Inc, Summary Basis of Approval, Apr. 12, 1999.
Blair, S., et al., *Skin sensitization potential of porcine gelatin, BOTOX® and BTXA in the guinea pig*, Journal of Clinical Neuroscience, 2004; 22(Suppl 1):S103-S104.
Boldyrev, International Journal of Biochemistry, 1990; 22(2):129-132.
Botox Label and Approval History for Botox Cosmetic BLA No. 103000, Approved Apr. 12, 2000, www.accessdata.fda.gov/scripts/cder/drugsatfda/index.cfm?fuseaction=Search.Label_Approval History, printed Jan. 27, 2006.
Bowen, American Journal of Veterinary Research, 1974; 35(5):661-668.
Brewster et al., *The Potential Use of Cyclodextrins in Parenteral Formulations*, J Parenter Sci Technol. 1989 Sep.-Oct.;43(5):231-40.
Brin, M.F., et al., *Botulinum Toxin: Dangerous Terminology Errors*, Journal of the Royal Society of Medicine, Aug. 1993; 86:493-494.
British Pharmacopoeia, *Hydroxyethylcellulose*, 1999; 766-768.
Brochure: CALBIOCHEM®, Neurotoxin Type A, *Clostridium Botulinum*, Revised: Sep. 28, 1999.
Budsberg, et al., AJVR, Dec. 1996; 57(12).
Carruthers, Alastair & Jean, *Toxins 99, New Information About the Botulinum Neurotoxins*, Dermatologic Surgery, 2000; 26(3):174-176.
Chuang, et al., *Pharmaceutical Strategies Utilizing Recombinant Human Serum Albumin*, Pharmaceutical Research, May 2002; 19(5):569-577.
Cohen and Thompson, *Use of Botulinum Toxin to Lateralize True Vocal Cords: A Biochemical Method to Relieve Bilateral Abductor Vocal Cord Paralysis*, Annals of Otology, Rhinology and Laryngology, 1987; 96(5):534-541.
Creighton, Thomas E., *Protein Structure: A Practical Approach*, 1989; 184-186.
Creighton, Thomas E., *Proteins: Structures and Molecular Properties*, 1984; 314-315.
Dodsworth, et al., *Comparative studies of recombinant human albumin and human serum albumin derived by blood fractionation*, Biotechnology and Applied Biochemistry, 1996; 24(2):171-176.
Encinar, et al., FEBS Letters, 1998, 429:78.
European Pharmacopoeia, *Hydroxyethylcellulose*, 1999; printed off CD-ROM:1-7.
Farrugia, C.A., et al., *Gelatin Denaturation and Renaturation Processes in Solution*, Pharmaceutical Research, 1997; 14:S-160.

Gartlan, M.G., et al., *Crystalline Preparation of Botulinum Toxin Type A (Botox): Degradation in Potency with Storage, Otolaryngology*—Head and Neck Surgery, Feb. 1993; 108(2):135-140.

Gassner, et al., Plastic and Reconstructive Surgery, 2000; 105(6):1948-1955.

Gibson, Jr., et al., International Journal of Pediatric Otorhinolaryngology, Jan. 1994; 28(2-3):Abstract only.

Giebink, Vaccine, 2001; 19:S129-S133.

Göbel, H., et al., *Evidence-based Medicine: Botulinum Toxin A in Migraine and Tension-Type Headache*, Journal of Neurology, 2001; 248(Suppl 1):1/34-1/38.

Gui, et al., *Botulinum Toxin Injected in the Gastric Wall Reduces Body Weight and Food Intake in Rats*, Alimentary Pharmacology & Therapeutics, 2000; 14(6):829-834.

Harlow, et al., *Antibodies A Laboratory Manual*, 1998; 66-67.

Hawthorne, et al., Journal of the American Animal Hospital Association, 1999; 35(2):135-146.

Heckmann, M., et al., *Botulinum Toxin A for Axillary Hyperhidrosis(Excessive Sweating)*, New England Journal of Medicine, Feb. 15, 2001; 344(7):488-492.

Hermeling, S., et al., *Antibody response to aggregated human interferon alpha2b in wild-type and transgenic immune tolerant mice depends on type and level of aggregation*, Journal of Pharmaceutical Sciences, May 2006; 95(5):1084-1096.

Hickford, et al., Journal of Small Animal Practice, 1998; 39(6):281-285.

Hoogerwerf, W.A., et al., *Botulinum Toxin for Spastic Gastrointestinal Disorders, Baillière's Clinical Gastroenterology*, 1999; 13(1):131-143.

Horn, et al., *Botulinum Toxin Paralysis of the Orbicularis Oculi Muscle. Types and Time Course of Alterations in Muscle Structure, Physiology and Lid Kinematics*, Experimental Brain Research, 1993; 96(1):39-53.

Inagi, et al., *Physiologic Assessment of Botulinum Toxin Effects in the Rat Larynx*, Laryngocope, 1998; 108(7):1048-1054.

Jankovic, J. et al., *Therapeutic Uses of Botulinum Toxin*, New England Journal of Medicine, Apr. 25, 1991;324(17):1186-94.

Jameel, F. et al., PDA Journal of Pharmaceutical Science & Technology, 39(3): 127-131 (May-Jun. 1995).

Jost and Kohl, *Botulinum Toxin: Evidence-Based Medicine Criteria in Rare Indications*, Journal of Neurology, 2001; 248(Suppl 1):1/39-1/44.

Jost, W.H., *Ten Years' Experience with Botulinum Toxin in Anal Fissure*, International Journal of Colorectal Disease, 2002; 17:298-302.

Kaplan and Pesce, *Clinical Chemistry, Theory, Analysis and Correlation*, The C.V. Mosby Company, 1984; 924-926.

Kobayashi, K., et al., *The Development of Recombinant Human Serum Albumin*, Therapeutic Apheresis, 1998; 2(4):257-262.

Label, 14-7683-006, Bayer Corporation, *Albumin (Human) 20% USP Plasbumin*—May 20, 1998.

Mahant, N., et al., *The Current Use of Botulinum Toxin*, Journal of Clinical Neuroscience, 2000; 7(5):389-394.

Marjama-Lyons, J., et al., *Tremor-Predominant Parkinson's Disease*, Drugs & Aging, Apr. 2000; 16(4):273-278.

Material Safety Data Sheet, Product #434965, Printed Aug. 9, 1999:5 pages.

McLellan, et al., Toxicon, 1996; 34(9):975-985.

McNally, *Protein Formulation and Delivery*, Marcel Dekker, Inc., New York, p. 145, 2000.

Melling, J., et al., *Clostridium Botulinum Toxins: Nature and Preparation for Clinical Use*, Eye, 1988; 2:16-23.

Meltzer, et al., Journal of Allergy and Clinical Immunology, 2000; 106(4).

Naumann, M., et al., *Botulinum toxin type A in the treatment of focal, axillary and palmar hyperhidrosis and other hyperhidrotic conditions*, European Journal of Neurology, 1999; 6(suppl 4):S111-S115.

Nosoh, Y., et al., *Protein Stability and Stabilization through Protein Engineering*, 1991; 197.

Ohtani, et al., *Structure of recombinant human serum albumin from Pichia pastoris*, Yakugaku Zasshi, 1997; 117(12):1033.

Ohtani, W., et al., *Physicochemical and Immunochemical Properties of Recombinant Human Serum Albumin from Pichia Pastoris*, Analytical Biochemistry, 1998; (256):56-62, Article No. AB972480.

Olsen D., et al., *Development of Recombinant Human Gelatins and Specific Molecular Type Human Gelatins*, Cambridge Healthtech Institute's $2^{nd}$ Annual International Transmisible Spongiform Encephalopathies (TSE Issues) in Alexandria, VA, Oct. 2-3, 2000.

Olsen, D., et al., *Expression and characterization of a low molecular weight recombinant human gelatin: development of a substitute for animal derived gelatin with superior features*, Journal of Protein Expression & Purification, 2005; 40:346-357.

Olsen, D., et al., *Expression and Characterization of Recombinant Human Gelatin Fragments*, American Association of Pharmaceutical Scientists (AAPS), Annual Meeting and Exposition, Indianapolis, Indiana, Oct. 29-Nov. 2, 2000.

Olsen, D., et al., *Recombinant collagen and gelatin for drug delivery*, Advanced Drug Delivery Reviews, Nov. 28, 2003; 55(12):1547-1567.

Olsen, R., et al., *Development of Recombinant Human Gelatin for Use as a Stabilizer in Biopharmaceuticals*, Formulation Strategies for Biopharmaceuticals, Philadelphia, PA, Sep. 22-24, 2003.

Package Insert Y36-002-345, DuPont Pharma, HESPAN®, 2 pages.

Patten, P.A., et al., *The immunogenicity of biopharmaceuticals. Lessons learned and consequences for protein drug development*, Journal of Developmental Biology (Basel), 2003; 112:81-97.

Pearce, et al., Toxicon, 1995; 33:217-227.

Pearce, et al., Journal of the Royal Society of Medicine, 1995; 88:239-240.

Peters, T., Jr., *All About Albumin Biochemistry, Genetics and Medical Applications*, Chapter 7, *Practical Aspects: Albumin in the Laboratory*, Academic Press, 1996; 295, 298-305.

Polysaccharides, Article from de.wikipedia.org, printed Jan. 26, 2006.

Porta, M., et al., *The Rationale and Results of Treating Muscle Spasm and Myofascial Syndromes with Botulinum Toxin Type A*, Pain Digest, 1998; 8(6):346-352.

Porter, C.J.H., *Drug Delivery to the Lymphatic System*, Critical Reviews™ in Therapeutic Drug Carrier Systems, 1997; 14(4):333-393.

Rader, R.A., *Botulinum toxin A, BIOPHARMA: Biopharmaceutical Products in the U.S. Market*, Ronald Rader, ed., Rockville, MD: Biotechnology Information Institute, 2001; 332:271-274.

Rader, R.A., *Botulinum toxin B, BIOPHARMA: Biopharmaceutical Products in the U.S. Market*, Ronald Rader, ed., Rockville, MD: Biotechnology Information Institute, 2001; 333:274-276.

Ragona, R.M., et al., *Management of the Parotid Sialocele with Botulinum Toxin*, Laryngoscope, Aug. 1999; 109(8):1344-1346.

Reichel, G., *Botulinum Toxin for Treatment of Spasticity in Adults*, Journal of Neurology, 2001; 248(Suppl 1):Jan. 25-Jan. 27.

Rollnik, J.D., et al., *Low-dose treatment of cervical dystonia, blepharospasm and facial hemispasm with albumin-diluted botulinum toxin type A under EMG Guidance*, European Neurology, 2000; 43:9-12.

Saliola, M., et al., *Use of the KlADH4 Promoter for Ethanol-Dependent Production of Recombinant Human Serum Albumin in Kluyveromyces lactis*, Applied Environmental Microbiology, Jan. 1999; 65(1):53-60.

Schantz, E.J., et al., *Standardized Assay for Clostridium Botulinum Toxins*, Journal of the AOAC, 1978; 61(1):96-99.

Schantz, E.J., *Use of Crystalline Type A Botulinum Toxin in Medical Research*, Biomedical Aspects of Botulism, Academic Press, 1981; 143-150.

Sesardic, et al., Biologicals, 2003; 31:265-276.

Sheridan, R., *Comparison of In Vivo and In Vitro Mouse Bioassays for Botulinum Toxin Antagonists*, Journal of Applied Toxicology, 1999; 19:S29-S33.

Sigma 1999 Catalog, *Biochemicals and Reagents for Life Science Research*, 187-188, 237.

Silberstein, S., et al., *Botulinum Toxin Type A as a Migraine Preventive Treatment*, Headache, 2000; 40:445-450.

Simpson, D., *Treatment of Spasticity with Botulinum Toxin*, Muscle & Nerve, Apr. 2000; 447-449.

Sloop, Richard R., et al., *Reconstituted botulinum toxin type A does not lose potency in humans if it is refrozen or refrigerated for 2 weeks before use*, Neurology, Jan. 1997; 48:249-253.

Storr and Allescher, *Esophageal Pharmacology and Treatment of Primary Motility Disorders, Diseases of the Esophagus*, 1999; 12:241-257.

Summary Basis of Approval, Apr. 12, 1999, OB-NDA 20-0952, 4 pages.

Szokoloczy, Magyar Allatorvosok Lapja, 1980; 35(6):423-426.

Tabita, et al., Jpn J Med Sci Biol, 1990; 43:219-231.

Tarelli, et al., *Recombinant human albumin as a stabilizer for biological materials and for the preparation of international reference reagents*, Biologicals, 1998; 26(4):331-346.

Tsuda, M., et al., In Vivo *Pathway of Thermal Hyperalgesia by Intrathecal Administration of α,β-methylene ATP in Mouse Spinal Cord: Involvement of the Glutamate-NMDA Receptor System*, British Journal of Pharmacology, 1999; 127(2):449-456.

The United States Pharmacopeia, the National Formulary, USP 24-NF 19, 2000, Supp. 10, *Hydroxyethyl Cellulose*.

Wohlfarth, H., et al., *Effect of Dilution on Activity of Commercial Preparations of Botulinum Toxin A in Man*, Society for Neuroscience, 1997; 23(870.11):2234.

Yang, C., et al., *Development of a recombinant human collagen-type III based hemostat*, Journal of Biomedical Materials Research, Apr. 15, 2004; 69B(1); 18-24.

Yang, C., et al., *The application of recombinant human collagen in tissue engineering*, BioDrugs, 2004; 18(2):103-119.

Yoneda, Shinji, et al., *Comparison of the therapeutic indexes of different molecular forms of botulinum toxin type A*, European Journal of Pharmacology, 2005; 508:223-229.

Zhang, et al., Gene, 2003; 315:21-32.

\* cited by examiner

POLYSACCHARIDE CONTAINING BOTULINUM TOXIN PHARMACEUTICAL COMPOSITIONS AND USES THEREOF

CROSS REFERENCE

This application is a continuation of application Ser. No. 10/359,828, filed Feb. 7, 2003, which is a continuation in part of application Ser. No. 10/288,738, filed Nov. 5, 2002, which is a continuation in part of application Ser. No. 10/047,058, filed Jan. 14, 2002 now abandoned, which is a continuation in part of application Ser. No. 09/500,147, filed Feb. 8, 2000 (now abandoned). The entire contents of these prior patent applications are incorporated herein by reference.

FIELD OF THE INVENTION

This invention relates to pharmaceutical compositions comprising a polysaccharide and a botulinum toxin, and uses thereof, such as to treat a facial wrinkle

BACKGROUND

The present invention relates to Clostridial toxin pharmaceutical compositions. In particular, the present invention relates to Clostridial toxin pharmaceutical compositions with a reduced toxicity and/or a reduced antigenicity and uses thereof.

A pharmaceutical composition is a formulation which contains at least one active ingredient (such as a Clostridial toxin) as well as, for example, one or more excipients, buffers, carriers, stabilizers, preservatives and/or bulking agents, and is suitable for administration to a patient to achieve a desired diagnostic result or therapeutic effect. The pharmaceutical compositions disclosed herein have diagnostic, therapeutic and/or research utility.

For storage stability and convenience of handling, a pharmaceutical composition can be formulated as a lyophilized (i.e. freeze dried) or vacuum dried powder which can be reconstituted with a suitable fluid, such as saline or water, prior to administration to a patient. Alternately, the pharmaceutical composition can be formulated as an aqueous solution or suspension. A pharmaceutical composition can contain a proteinaceous active ingredient. Unfortunately, a protein active ingredient can be very difficult to stabilize (i.e. maintained in a state where loss of biological activity is minimized), resulting therefore in a loss of protein and/or loss of protein activity during the formulation, reconstitution (if required) and during the period of storage prior to use of a protein containing pharmaceutical composition. Stability problems can occur because of protein denaturation, degradation, dimerization, and/or polymerization. Various excipients, such as albumin and gelatin have been used with differing degrees of success to try and stabilize a protein active ingredient present in a pharmaceutical composition. Additionally, cryoprotectants such as alcohols have been used to reduce protein denaturation under the freezing conditions of lyophilization.

Albumin

Albumins are small, abundant plasma proteins. Human serum albumin has a molecular weight of about 69 kiloDaltons (kD) and has been used as a non-active ingredient in a pharmaceutical composition where it can serve as a bulk carrier and stabilizer of certain protein active ingredients present in a pharmaceutical composition.

The stabilization function of albumin in a pharmaceutical composition can be present both during the multi-step formulation of the pharmaceutical composition and upon the later reconstitution of the formulated pharmaceutical composition. Thus, stability can be imparted by albumin to a proteinaceous active ingredient in a pharmaceutical composition by, for example, (1) reducing adhesion (commonly referred to as "stickiness") of the protein active ingredient to surfaces, such as the surfaces of laboratory glassware, vessels, to the vial in which the pharmaceutical composition is reconstituted and to the inside surface of a syringe used to inject the pharmaceutical composition. Adhesion of a protein active ingredient to surfaces can lead to loss of active ingredient and to denaturation of the remaining retained protein active ingredient, both of which reduce the total activity of the active ingredient present in the pharmaceutical composition, and; (2) reducing denaturation of the active ingredient which can occur upon preparation of a low dilution solution of the active ingredient.

As well as being able to stabilize a protein active ingredient in a pharmaceutical composition, human serum albumin also has the advantage of generally negligible immunogenicity when injected into a human patient. A compound with an appreciable immunogenicity can cause the production of antibodies against it which can lead to an anaphylactic reaction and/or to the development of drug resistance, with the disease or disorder to be treated thereby becoming potentially refractory to the pharmaceutical composition which has an immunogenic component.

Unfortunately, despite its known stabilizing effect, significant drawbacks exist to the use of human serum albumin in a pharmaceutical composition. For example human serum albumins are expensive and increasingly difficult to obtain. Furthermore, blood products such as albumin, when administered to a patient can subject the patient to a potential risk of receiving blood borne pathogens or infectious agents. Thus, it is known that the possibility exists that the presence of albumin in a pharmaceutical composition can result in inadvertent incorporation of infectious elements into the pharmaceutical composition. For example, it has been reported that use of human serum albumin may transmit prions into a pharmaceutical composition. A prion is a proteinaceous infectious particle which is hypothesized to arise as an abnormal conformational isoform from the same nucleic acid sequence which makes the normal protein. It has been further hypothesized that infectivity resides in a "recruitment reaction" of the normal isoform protein to the prion protein isoform at a post translational level. Apparently the normal endogenous cellular protein is induced to misfold into a pathogenic prion conformation. Significantly, several lots of human serum albumin have been withdrawn from distribution upon a determination that a blood donor to a pool from which the albumin was prepared was diagnosed with Creutzfeldt-Jacob disease.

Creutzfeldt-Jacob disease (sometimes characterized as Alzheimer's disease on fast forward) is a rare neurodegenerative disorder of human transmissible spongiform encephalopathy where the transmissible agent is apparently an abnormal isoform of a prion protein. An individual with Creutzfeldt-Jacob disease can deteriorate from apparent perfect health to akinetic mutism within six months. Possible iatrogenic transmission of Creutzfeldt-Jacob disease by human serum albumin transfusion has been reported and it has been speculated that sufficient protection against Creutzfeldt-Jacob disease transmission is not provided by the usual methods of human serum albumin preparation which methods include disposal of blood cellular elements and heating to 60 degrees C. for 10 hours. Thus, a potential risk may exist of acquiring a prion mediated disease, such as Creutzfeldt-Jacob disease, from the administration of a pharmaceutical composition which contains human plasma protein concentrates, such as serum albumin.

Gelatin has been used in some protein active ingredient pharmaceutical compositions as an albumin substitute. Notably, gelatin is a animal derived protein and therefore carries the same risk of potential infectivity which may be possessed by human serum albumin. Hence, it is desirable to find a substitute for human serum albumin which is not a blood fraction, and preferably, the albumin substitute is not gelatin and is not derived from any animal (i.e. mammalian) source.

Collagen has been used cosmetically as a filler material to treat of skin contour problems, such as to smooth smile line grooves and frown lines, folds between the eyebrows, wrinkles in the corners of the eyes and fine vertical creases above and below the lips. Collagen is also useful in smoothing certain post-surgical traumatic or acne scarring and viral pock marks, such as chicken pox marks. For such purposes the collagen is injected into the dermis to raise the skin.

Botulinum toxin

The genus *Clostridium* has more than one hundred and twenty seven species, grouped by morphology and function. The anaerobic, gram positive bacterium *Clostridium botulinum* produces a potent polypeptide neurotoxin, botulinum toxin, which causes a neuroparalytic illness in humans and animals referred to as botulism. *Clostridium botulinum* and its spores are commonly found in soil and the bacterium can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of botulinum toxin (purified neurotoxin complex) type A is a $LD_{50}$ in mice. Interestingly, on a molar basis, botulinum toxin type A is 1.8 billion times more lethal than diphtheria, 600 million times more lethal than sodium cyanide, 30 million times more lethal than cobrotoxin and 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated $LD_{50}$ of botulinum toxin type A is of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18-20 grams each. In other words, one unit of botulinum toxin is the amount of botulinum toxin that kills 50% of a group of female Swiss Webster mice. Seven generally immunologically distinct botulinum neurotoxins have been characterized, these being respectively botulinum neurotoxin serotypes A, B, $C_1$, D, E, F, and G, each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. The botulinum toxins apparently bind with high affinity to cholinergic motor neurons, are translocated into the neuron and block the presynaptic release of acetylcholine.

Botulinum toxins have been used in clinical settings for the treatment of neuromuscular disorders characterized by hyperactive skeletal muscles. Botulinum toxin type A was approved by the U.S. Food and Drug Administration in 1989 for the treatment of essential blepharospasm, strabismus and hemifacial spasm in patients over the age of twelve. Clinical effects of peripheral injection (i.e. intramuscular or subcutaneous) botulinum toxin type A are usually seen within one week of injection, and often within a few hours after injection. The typical duration of symptomatic relief (i.e. flaccid muscle paralysis) from a single intramuscular injection of botulinum toxin type A can be about three months to about six months.

Although all the botulinum toxins serotypes apparently inhibit release of the neurotransmitter acetylcholine at the neuromuscular junction, they do so by affecting different neurosecretory proteins and/or cleaving these proteins at different sites. Botulinum toxin A is a zinc endopeptidase which can specifically hydrolyze a peptide linkage of the intracellular, vesicle associated protein SNAP-25. Botulinum type E also cleaves the 25 kiloDalton (kD) synaptosomal associated protein (SNAP-25), but targets different amino acid sequences within this protein, as compared to botulinum toxin type A. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain (H chain) and a cell surface receptor; the receptor is thought to be different for each serotype of botulinum toxin and for tetanus toxin. The carboxyl end segment of the H chain, $H_c$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of botulinum toxin activity appears to involve reduction of the disulfide bond joining the H and L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin B, D, F, and G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ are apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemagglutinin protein and a non-toxin and non-toxic nonhemagglutinin protein. These two non-toxin proteins (which along with the botulinum toxin molecule can comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex. The toxin complexes can be dissociated into toxin protein and hemagglutinin proteins by treating the complex with red blood cells at pH 7.3. The toxin protein has a marked instability upon removal of the hemagglutinin protein.

All the botulinum toxin serotypes are made by *Clostridium botulinum* bacteria as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D, and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

High quality crystalline botulinum toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Schantz process can be used to obtain crystalline botulinum toxin type A, as set forth in Schantz, E. J., et al, *Properties and use of Botulinum toxin and Other Microbial Neurotoxins in Medicine*, Microbiol Rev. 56: 80-99 (1992). Generally, the botulinum toxin type A complex can be isolated and purified from an anaerobic fermentation by cultivating *Clostridium botulinum* type A in a suitable medium. Raw toxin can be harvested by precipitation with sulfuric acid and concentrated by ultramicrofiltration. Purification can be carried out by dissolving the acid precipitate in calcium chloride. The toxin can then be precipitated with cold ethanol. The precipitate can be dissolved in sodium phosphate buffer and centrifuged. Upon drying there can then be obtained approximately 900 kD crystalline botulinum toxin type A complex with a specific potency of $3 \times 10^7$ $LD_{50}$ U/mg or greater. This known process can also be used, upon separation out of the non-toxin proteins, to obtain pure botulinum toxins, such as for example: purified botulinum toxin type A with an approximately 150 kD molecular weight with a specific potency of 1-2×$10^8$ $LD_{50}$ U/mg or greater; purified botulinum toxin type B with an approximately 156 kD molecular weight with a specific potency of 1-2×$10^8$ $LD_{50}$ U/mg or greater, and; purified botulinum toxin type F with an approximately 155 kD molecular weight with a specific potency of 1-2×$10^7$ $LD_{50}$ U/mg or greater.

Botulinum toxins and toxin complexes can be obtained from, for example, List Biological Laboratories, Inc., Campbell, Calif.; the Centre for Applied Microbiology and Research, Porton Down, U.K.; Wako (Osaka, Japan), as well as from Sigma Chemicals of St Louis, Mo. Commercially available botulinum toxin containing pharmaceutical compositions include BOTOX® (Botulinum toxin type A neurotoxin complex with human serum albumin and sodium chloride) available from Allergan, Inc., of Irvine, Calif. in 100 unit vials as a lyophilized powder to be reconstituted with 0.9% sodium chloride before use), Dysport® (*Clostridium botulinum* type A toxin haemagglutinin complex with human serum albumin and lactose in the formulation), available from Ipsen Limited, Berkshire, U.K. as a powder to be reconstituted with 0.9% sodium chloride before use), and MyoBloc™ (an injectable solution comprising botulinum toxin type B, human serum albumin, sodium succinate, and sodium chloride at about pH 5.6, available from Elan Corporation, Dublin, Ireland).

The success of botulinum toxin type A to treat a variety of clinical conditions has led to interest in other botulinum toxin serotypes. Additionally, pure botulinum toxin has been used to treat humans. see e.g. Kohl A., et al., *Comparison of the effect of botulinum toxin A (Botox(R)) with the highly-purified neurotoxin (NT 201) in the extensor digitorum brevis muscle test*, Mov Disord 2000; 15(Suppl 3):165. Hence, a pharmaceutical composition can be prepared using a pure botulinum toxin.

The type A botulinum toxin is known to be soluble in dilute aqueous solutions at pH 4-6.8. At pH above about 7 the stabilizing nontoxic proteins dissociate from the neurotoxin, resulting in a gradual loss of toxicity, particularly as the pH and temperature rise. Schantz E. J., et al *Preparation and characterization of botulinum toxin type A for human treat-*

*ment* (in particular pages 44-45), being chapter 3 of Jankovic, J., et al, *Therapy with Botulinum Toxin*, Marcel Dekker, Inc (1994).

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

It has been reported that BoNt/A has been used in various clinical settings, including as follows:

(1) about 75-125 units of BOTOX®[1] per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

[1] Available from Allergan, Inc., of Irvine, Calif. under the tradename BOTOX®.

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Supp 4): S111-S1150:1999), and in some circumstances for as long as 27 months. *The Laryngoscope* 109:1344-1346:1999. However, the usual duration of an intramuscular injection of Botox® is typically about 3 to 4 months.

The success of botulinum toxin type A to treat a variety of clinical conditions has led to interest in other botulinum toxin serotypes. Additionally, pure botulinum toxin has been used in humans. see e.g. Kohl A., et al., *Comparison of the effect of botulinum toxin A (Botox (R)) with the highly-purified neurotoxin (NT 201) in the extensor digitorum brevis muscle test*, Mov Disord 2000; 15(Suppl 3): 165 Hence, a pharmaceutical composition can be prepared using a pure botulinum toxin.

The botulinum toxin molecule (about 150 kDa), as well as the botulinum toxin complexes (about 300-900 kDa), such as the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) are dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin must be stabilized with a stabilizing agent. To date, the only successful stabilizing agent for this purpose has been the animal derived proteins human serum albumin and gelatin. And as indicated, the presence of animal derived proteins in the final formulation presents potential problems in that certain stable viruses, prions, or other infectious or pathogenic compounds carried through from donors can contaminate the toxin.

Furthermore, any one of the harsh pH, temperature and concentration range conditions required to lyophilize (freeze-dry) or vacuum dry a botulinum toxin containing pharmaceutical composition into a toxin shipping and storage format (ready for use or reconstitution by a physician) can detoxify the toxin. Thus, animal derived or donor pool proteins such as gelatin and serum albumin have been used with some success to stabilize botulinum toxin.

A commercially available botulinum toxin containing pharmaceutical composition is sold under the trademark BOTOX® (available from Allergan, Inc., of Irvine, Calif.). BOTOX® consists of a purified botulinum toxin type A complex, human serum albumin, and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of *Clostridium botulinum* toxin type A complex, 0.5 milligrams of human serum albumin and 0.9 milligrams of sodium chloride in a sterile, vacuum-dried form without a preservative.

To reconstitute vacuum-dried BOTOX® sterile normal saline without a preservative (0.9% Sodium Chloride injection) is used by drawing up the proper amount of diluent in the appropriate size syringe. Since BOTOX® is denatured by bubbling or similar violent agitation, the diluent is gently injected into the vial. For sterility reasons, BOTOX® should be administered within four hours after reconstitution. During this time period, reconstituted BOTOX® is stored in a refrigerator (2° to 8° C.). Reconstituted BOTOX® is clear, colorless and free of particulate matter. The vacuum-dried product is stored in a freezer at or below −5° C.

It has been reported that a suitable alternative to human serum albumin as a botulinum toxin stabilizer may be another protein or alternatively a low molecular weight (non-protein) compound. Carpender et al., *Interactions of Stabilizing Additives with Proteins During Freeze-Thawing and Freeze-Drying*, International Symposium on Biological Product Freeze-Drying and Formulation, 24-26 October 1990; Karger (1992), 225-239.

Many substances commonly used as carriers and bulking agents in pharmaceutical compositions have proven to be unsuitable as albumin replacements in a Clostridial toxin containing pharmaceutical composition. For example, the disaccharide cellobiose has been found to be unsuitable as a botulinum toxin stabilizer. Thus, it is known that the use of cellobiose as an excipient in conjunction with albumin and sodium chloride results in a much lower level of toxicity (10% recovery) after lyophilization of crystalline botulinum toxin type A with these excipients, as compared to the toxicity after lyophilization with only human serum albumin (>75% to >90% recovery). Goodnough et al., *Stabilization of Botulinum Toxin Type A During Lyophilization*, App & Envir. Micro. 58 (10) 3426-3428 (1992).

Furthermore, saccharides, including polysaccharides, are in general poor candidates to serve as protein stabilizers. Thus, it is known that a pharmaceutical composition containing a protein active ingredient is inherently unstable if the protein formulation comprises a saccharide (such as glucose or a polymer of glucose) or carbohydrates because proteins and glucose are known to interact together and to undergo the well-described Maillard reaction, due to the reducing nature of glucose and glucose polymers. Much work has been dedicated to mostly unsuccessful attempts at preventing this protein-saccharide reaction by, for example, reduction of moisture or use of non-reducing sugars. Significantly, the degradative pathway of the Maillard reaction can result in a therapeutic insufficiency of the protein active ingredient. A pharmaceutical formulation comprising protein and a reducing saccharide, carbohydrate or sugar, such as a glucose polymer, is therefore inherently unstable and cannot be stored for a long period of time without significant loss of the active ingredient protein's desired biological activity.

Notably, one of the reasons human serum albumin can function effectively as a stabilizer of a protein active ingredient in a pharmaceutical composition is because, albumin, being a protein, does not undergo the Maillard reaction with the protein active ingredient in a pharmaceutical composition. Hence, one would expect to find and to look for a substitute for human serum albumin amongst other proteins.

Finding an appropriate substitute for human serum albumin as a stabilizer of the botulinum toxin present in a pharmaceutical composition is difficult and problematic because human serum albumin is believed to function in a pharmaceutical composition as more than a mere bulking agent. Thus, albumin apparently can interact with botulinum toxin so as to increase the potency of the neurotoxin. For example, it is known that bovine serum albumin can act as more than a mere stabilizing excipient for botulinum toxin type A, since bovine serum albumin apparently also accelerates the rate of catalysis of synthetic peptide substrates, which substrates resemble the SNAP-25 intraneuronal substrate for botulinum toxin type A Schmidt, et al., *Endoproteinase Activity of Type A Botulinum Neurotoxin Substrate Requirements and Activation by Serum Albumin*, J. of Protein Chemistry, 16 (1), 19-26 (1997). Thus, albumin may have a potentiating effect, apparently by affecting rate kinetics, upon the intracellular proteolytic action of a botulinum toxin upon the toxin's substrate. This potentiating effect may be due to albumin which has accompanied the botulinum toxin upon endocytosis of the toxin into a target neuron or the potentiating effect may be due to the pre-existing presence cytoplasmic albumin within the neuron protein prior to endocytosis of the botulinum toxin.

The discovery of the presence of a kinetic rate stimulatory effect by bovine serum albumin upon the proteolytic activity of botulinum toxin type A renders the search for a suitable substitute for albumin in a botulinum toxin containing pharmaceutical formulation especially problematic. Thus, an albumin substitute with desirable toxin stabilization characteristics may have an unknown and possibly deleterious effect upon the rate of substrate catalysis by the toxin, since at least with regard to bovine serum albumin the two characteristics (toxin stabilization and toxin substrate catalysis potentiation) are apparently inherent to the same albumin excipient. This potentiating effect of albumin shows that albumin does not act as a mere excipient in the formulation and therefore renders the search for a suitable substitute for albumin more difficult.

Additionally there are many unique characteristics of botulinum toxin and its formulation into a suitable pharmaceutical composition which constrain and hinder and render the search for a replacement for the albumin used in current botulinum toxin containing pharmaceutical formulations very problematic. Examples of four of these unique characteristics follow.

First, botulinum toxin is a relatively large protein for incorporation into a pharmaceutical formulation (the molecular weight of the botulinum toxin type A complex is 900 kD) and is therefore is inherently fragile and labile. The size of the toxin complex makes it much more friable and labile than smaller, less complex proteins, thereby compounding the formulation and handling difficulties if toxin stability is to be maintained. Hence, an albumin replacement must be able to interact with the toxin in a manner which does not denature, fragment or otherwise detoxify the toxin molecule or cause disassociation of the non-toxin proteins present in the toxin complex.

Second, as the most lethal known biological product, exceptional safety, precision, and accuracy is called for at all steps of the formulation of a botulinum toxin containing pharmaceutical composition. Thus, a preferred potential albumin replacer should not itself be toxic or difficult to handle so as to not exacerbate the already extremely stringent botulinum toxin containing pharmaceutical composition formulation requirements.

Third, since botulinum toxin was the first microbial toxin to be approved (by the FDA in 1989) for injection for the treatment of human disease, specific protocols had to be developed and approved for the culturing, bulk production, formulation into a pharmaceutical and use of botulinum toxin. Important considerations are toxin purity and dose for injection. The production by culturing and the purification must be carried out so that the toxin is not exposed to any substance that might contaminate the final product in even trace amounts and cause undue reactions in the patient. These restrictions require culturing in simplified medium without the use of animal meat products and purification by procedures not involving synthetic solvents or resins. Preparation of toxin using enzymes, various exchangers, such as those present in chromatography columns and synthetic solvents can introduce contaminants and are therefore excluded from preferred formulation steps. Furthermore, botulinum toxin type A is readily denatured at temperatures above 40 degrees C., loses toxicity when bubbles form at the air/liquid interface, and denatures in the presence of nitrogen or carbon dioxide.

Fourth, particular difficulties exist to stabilize botulinum toxin type A, because type A consists of a toxin molecule of about 150 kD in noncovalent association with nontoxin proteins weighing about 750 kD. The nontoxin proteins are believed to preserve or help stabilize the secondary and tertiary structures upon which toxicity is dependant. Procedures or protocols applicable to the stabilization of nonproteins or to relatively smaller proteins are not applicable to the problems inherent with stabilization of the botulinum toxin complexes, such as the 900 kD botulinum toxin type A complex. Thus while from pH 3.5 to 6.8 the type A toxin and non toxin proteins are bound together noncovalently, under slightly alkaline conditions (pH>7.1) the very labile toxin is released from the toxin complex. As set forth previously, pure botulinum toxin (i.e. the 150 kD molecule) has been proposed as the active ingredient in a pharmaceutical composition.

In light of the unique nature of botulinum toxin and the requirements set forth above, the probability of finding a suitable albumin replacement for the human serum albumin used in current botulinum toxin containing pharmaceutical compositions must realistically be seen to approach zero. Prior to the present invention, only the animal derived proteins, human serum albumin and gelatin, had been known to have utility as suitable stabilizers of the botulinum toxin present in a pharmaceutical formulation. Thus, albumin, by itself or with one or more additional substances such as sodium phosphate or sodium citrate, is known to permit high recovery of toxicity of botulinum toxin type A after lyophilization. Unfortunately, as already set forth, human serum albumin, as a pooled blood product, can, at least potentially, carry infectious or disease causing elements when present in a pharmaceutical composition. Indeed, any animal product or protein such as human serum albumin or gelatin can also potentially contain pyrogens or other substances that can cause adverse reactions upon injection into a patient.

Chinese patent application CN 1215084A discusses an albumin free botulinum toxin type A formulated with gelatin, an animal derived protein. U.S. Pat. No. 6,087,327 also discloses a composition of botulinum toxin types A and B formulated with gelatin. These formulations therefore do not eliminate the risk of transmitting an animal protein derived or accompanying infectious element.

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153-9158: 1990.

As set forth above, foodborne botulism can result from swallowing botulinum toxin present in improperly preserved food. The toxin can pass unattenuated across gut mucosa into the general circulation and is carried by the bloodstream to peripheral cholinergic synapses where it blocks acetylcholine release causes impaired autonomic and neuromuscular transmission, one of the primary symptoms being flaccid muscle paralysis. Similarly ingestion or injection of tetanus toxin can result in the spastic paralysis characteristic of tetanus. As expected, intravenous administration of botulinum toxin causes botulism and can be fatal depending upon factors such as the dose of toxin administered and the condition of the patient. See e.g. Arnon, S. S., *Clinical Botulism*, chapter 13, pages 145-150 of Brin M. F. et al, editors, *Scientific and therapeutic aspects of botulinum Toxin*, Lippincoft, Williams & Wilkins (2002), and; Kondo H., et al, *Titration of botulinum toxins for lethal toxicity by intravenous injection into mice*, Jpn J Med Sci Biol 1984; 37:131-5.

Clinical use of botulinum toxin is typically by subcutaneous or intramuscular administration in order to treat, for example, a spastic muscle disorder or for the cosmetic alleviation of hyperkinetic facial wrinkles. Through errors or incompetence in physician administration technique, inadvertent overdosing and/or patient sensitivity to the toxin, iatrogenic intoxication, as revealed symptomatically by widespread muscle weakness, can occur.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephrine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

Hydroxyethyl Starch

A polysaccharide can be made up of hundreds or even thousands of monosaccharide units held together by glycoside (ether) linkages. Two important polysaccharides are cellulose and starch. Cellulose is the chief structural material in plants, giving plants their rigidity and form. Starch makes up the reserve food supply of plants and is found mainly in various seeds and tubers.

Starch occurs as granules whose size and shape are characteristic of the plant from which the starch is obtained. In general about 80% of starch is a water insoluble fraction called amylopectin. Amylopectin is made up of chains of D-glucose (as glucopyranose) units, each unit being joined by an alpha glycoside linkage to C-4 of the next glucose unit. Like starch, cellulose is also made up of chains of D-glucose units, where each unit is joined by a glucoside linkage to the C-4 of the next unit. Unlike starch though, the glycoside linkages in cellulose are beta linkages. Treatment of cellulose with sulfuric acid and acetic anhydride yields the disaccharide cellobiose. As previously set forth, attempts to stabilize botulinum toxin using cellobiose have been unsuccessful.

A particular starch derivative which can be obtained by treating starch with pyridine and ethylene chlorohydrin, is 2-hydroxyethyl starch, also called hetastarch. U.S. Pat. No. 4,457,916 discloses a combination of a nonionic surfactant and hydroxyethyl starch to stabilize aqueous solutions of tumor necrosis factor (TNF). Additionally, a 6% aqueous solution of 2-hydroxyethyl starch (hetastarch) (available from Dupont Pharma, Wilmington, Del. under the trade name HESPAN®, 6% hetastarch in 0.9% sodium chloride injection) is known. Albumin is known to act as a plasma volume expander upon intravenous administration to a patient. HESPAN® has also been administrated to patients to achieve a plasma volume expansion effect and in that sense intravenous HESPAN® can be considered a replacement for intravenous albumin.

Hetastarch is an artificial colloid derived from a waxy starch composed almost entirely of amylopectin. Hetastarch can be obtained by introducing hydroxyethyl ether groups onto glucose units of the starch, and the resultant material can then be hydrolyzed to yield a product with a molecular weight suitable for use as a plasma volume expander. Hetastarch is characterized by its molar substitution and also by its molecular weight. The molar substitution can be approximately 0.75, meaning that hetastarch is etherified to the extent that for every 100 glucose units of hetastarch there are, on average, approximately 75 hydroxyethyl substituent groups. The average molecular weight of hetastarch is approximately 670 kD with a range of 450 kD to 800 kD and with at least 80% of the polymer units falling within the range of 20 kD to 2,500 kD. Hydroxyethyl groups are attached by ether linkages primarily at C-2 of the glucose unit and to a lesser extent at C-3 and C-6. The polymer resembles glycogen, and the polymerized D-glucose units are joined primarily by α-1,4 linkages with occasional α-1,6 branching linkages. The degree of branching is approximately 1:20, meaning that there is an average of approximately one α-1,6 branch for every 20 glucose monomer units. Hetastarch is comprised of more than 90% amylopectin.

The plasma volume expansion produced by HESPAN® can approximate that obtained with albumin. Hetastarch molecules below 50 kD molecular weight are rapidly eliminated by renal excretion and a single dose of approximately 500 mL of HESPAN® (approximately 30 g) results in elimination in the urine of approximately 33% of the administered HESPAN® within about 24 hours. The hydroxyethyl group of hydroxyethyl starch is not cleaved in vivo, but remains intact and attached to glucose units when excreted. Significant quantities of glucose are not produced as hydroxyethylation prevents complete metabolism of the smaller hydroxyethyl starch polymers Cellulose can likewise be converted to a hydroxyethyl cellulose. The average molecular weight of 2-hydroxyethyl cellulose (a 2-hydroxyethyl ether of cellulose) is about 90 kD. Unfortunately, hydroxyethyl cellulose, unlike hydroxyethyl starch, is highly reactive and therefore unsuited for use as a stabilizer of a protein active ingredient in a pharmaceutical formulation.

What is needed therefore is a botulinum toxin containing pharmaceutical composition which is free of animal derived proteins such as a blood pooled or blood fraction derived serum albumin or gelatin and which has a reduced toxicity and/or a reduced antigenicity.

SUMMARY

The present invention meets this need and provides a botulinum toxin pharmaceutical composition which is free of animal derived proteins such as a blood pooled or blood fraction derived human serum albumin or gelatin, and which has a reduced toxicity and/or a reduced immunogenicity. One embodiment of the present invention is a botulinum toxin pharmaceutical composition wherein the primary stabilizer present in the formulation is a polysaccharide.

The present invention encompasses new pharmaceutical compositions, embodiments of which can provide a superior replacement (i.e. by use of a suitable polysaccharide, with or without additional stabilizers) for the serum or native albumin present as a primary stabilizer in a pharmaceutical composition. Thus, my invention encompasses new, stabilized botulinum toxin pharmaceutical compositions, which can have the additional and desirable characteristic of reduced toxicity, such as a reduced systemic toxicity (i.e. upon intravenous administration) or such as a reduced toxicity upon intramuscular administration. The serum or native albumin replacement compound used has the characteristic of low, and preferably negligible, immunogenicity when injected into a patient.

Definitions

As used herein, the words or terms set forth below have the following definitions.

"About" means that the item, parameter or term so qualified encompasses a range of plus or minus ten percent above and below the value of the stated item, parameter or term.

"Administration", or "to administer" means the step of giving (i.e. administering) a pharmaceutical composition to a subject. The pharmaceutical compositions disclosed herein are "locally administered" by e.g. intramuscular (i.m.), intradermal, subcutaneous administration, intrathecal administration, intraperitoneal (i.p.) administration, topical (transdermal) and implantation (i.e. of a slow-release device such as polymeric implant or miniosmotic pump) routes of administration.

"Amino acid" includes polyamino acids.

"Animal protein free" means the absence of blood derived, blood pooled and other animal derived products or compounds. "Animal" means a mammal (such as a human), bird, reptile, fish, insect, spider or other animal species. "Animal" excludes microorganisms, such as bacteria. Thus, an animal protein free pharmaceutical composition within the scope of my invention can include a Clostridial neurotoxin. For example, an animal protein free pharmaceutical composition means a pharmaceutical composition which is either substantially free or essentially free or entirely free of a serum derived albumin, gelatin and other animal derived proteins, such as immunoglobulins. An example of an animal protein free pharmaceutical composition is a pharmaceutical composition which comprises or which consists of a botulinum toxin (as the active ingredient) and a suitable polysaccharide as a stabilizer or excipient.

"Botulinum toxin" means a neurotoxin produced by *Clostridium botulinum*, as well as a botulinum toxin (or the light chain or the heavy chain thereof) made recombinantly by a non-Clostridial species. The phrase "botulinum toxin", as used herein, encompasses the botulinum toxin serotypes A, B, C, D, E, F and G. Botulinum toxin, as used herein, also encompasses both a botulinum toxin complex (i.e. the 300, 600 and 900 kDa complexes) as well as the purified botulinum toxin (i.e. about 150 kDa). "Purified botulinum toxin" is defined as a botulinum toxin that is isolated, or substantially isolated, from other proteins, including proteins that form a botulinum toxin complex. A purified botulinum toxin may be greater than 95% pure, and preferably is greater than 99% pure. The botulinum $C_2$ and $C_3$ cytotoxins, not being neurotoxins, are excluded from the scope of the present invention.

"Clostridial neurotoxin" means a neurotoxin produced from, or native to, a Clostridial bacterium, such as *Clostridium botulinum, Clostridium butyricum* or *Clostridium beratti*, as well as a Clostridial neurotoxin made recombinantly by a non-Clostridial species.

"Entirely free (i.e. "consisting of" terminology) means that within the detection range of the instrument or process being used, the substance cannot be detected or its presence cannot be confirmed.

"Essentially free" (or "consisting essentially of") means that only trace amounts of the substance can be detected.

"Immobilizing" means a step that prevents a subject from moving one or more body parts. If a sufficient number of body parts are immobilized, the subject will accordingly be immobilized. Thus, "immobilizing" encompasses the immobilization of a body part, such as a limb, and/or the complete immobilization of a subject.

"Modified botulinum toxin" means a botulinum toxin that has had at least one of its amino acids deleted, modified, or replaced, as compared to a native botulinum toxin. Additionally, the modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

"Patient" means a human or non-human subject receiving medical or veterinary care. Accordingly, as disclosed herein, the compositions may be used in treating any animal, such as mammals.

"Pharmaceutical composition" means a formulation in which an active ingredient can be a neurotoxin, such as a Clostridial neurotoxin. The word "formulation" means that there is at least one additional ingredient in the pharmaceutical composition besides a neurotoxin active ingredient. A pharmaceutical composition is therefore a formulation which is suitable for diagnostic or therapeutic administration (i.e. by intramuscular or subcutaneous injection or by insertion of a depot or implant) to a subject, such as a human patient. The pharmaceutical composition can be: in a lyophilized or vacuum dried condition; a solution formed after reconstitution of the lyophilized or vacuum dried pharmaceutical composition with saline or water, or; as a solution which does not require reconstitution. The neurotoxin active ingredient can be one of the botulinum toxin serotypes A, B, $C_1$, D, E, F or G or a tetanus toxin, all of which can be made natively by Clostridial bacteria. As stated, a pharmaceutical composition can be liquid or solid, for example vacuum-dried. The constituent ingredients of a pharmaceutical composition can be included in a single composition (that is all the constituent ingredients, except for any required reconstitution fluid, are present at the time of initial compounding of the pharmaceutical composition) or as a two-component system, for example a vacuum-dried composition reconstituted with a diluent such as saline which diluent contains an ingredient not present in the initial compounding of the pharmaceutical composition. A two-component system provides the benefit of allowing incorporation of ingredients which are not sufficiently compatible for long-term shelf storage with the first component of the two component system. For example, the reconstitution vehicle or diluent may include a preservative which provides sufficient protection against microbial growth for the use period, for example one-week of refrigerated storage, but is not present during the two-year freezer storage period during which time it might degrade the toxin. Other ingredients, which may not be compatible with a Clostridial toxin or other ingredients for long periods of time, may be incorporated in this manner; that is, added in a second vehicle (i.e. in the reconstitution fluid) at the approximate time of use.

"Polysaccharide" means a polymer of more than two saccharide molecule monomers, which monomers can be identical or different.

"Protein stabilizer" (or "primary stabilizer") is a chemical agent that assists to preserve or maintain the biological structure (i.e. the three dimensional conformation) and/or biological activity of a protein (such as a Clostridial neurotoxin, such as a botulinum toxin). Stabilizers can be proteins or polysaccharides. Examples of protein stabilizers include hydroxyethyl starch (hetastarch), serum albumin, gelatin, collagen, as well as a recombinant albumin, gelatin or collagen. As disclosed herein, the primary stabilizer can be a synthetic agent that would not produce an immunogenic response (or produces an attenuated immune response) in a subject receiving a composition containing the primary stabilizer. In other embodiments of the invention, the protein stabilizers may be proteins from the same species of animal that is being administered the protein. Additional stabilizers may also be included in a pharmaceutical composition. These additional or secondary stabilizers may be used alone or in combination with primary stabilizers, such as proteins and polysaccharides. Exemplary secondary stabilizers include, but are not limited to non-oxidizing amino acid derivatives (such as a tryptophan derivate, such as N-acetyl-tryptophan ("NAT")), caprylate (i.e. sodium caprylate), a polysorbate (i.e. P80), amino acids, and divalent metal cations such as zinc. A pharmaceutical composition can also include preservative agents such as benzyl alcohol, benzoic acid, phenol, parabens and sorbic acid. A "recombinant stabilizer" is a "primary stabilizer" made by recombinant means, such as for example, a recombinantly made albumin (such as a recombinantly made human serum albumin), collagen, gelatin or a cresol, such as an M-cresol.

"Reduced toxicity" means, with regard to a first pharmaceutical composition (i.e. Formulation II or IIA) with a particular protein active ingredient (i.e. a botulinum toxin) and a particular excipient or protein stabilizer, that the first pharmaceutical composition can be administered (i.e. by an intramuscular or intravenous route of administration) to a mammal at a dose level which is at the same as or even twice what is a fatal dose of a second pharmaceutical composition (i.e. Formulation I) administered by the same route, which second pharmaceutical composition has the same protein active ingredient (i.e. a botulinum toxin) but which does not have the same particular excipient or protein stabilizer, without death resulting to the mammal to which the first pharmaceutical composition is administered.

"Stabilizing", "stabilizes", or "stabilization" mean that a pharmaceutical active ingredient ("PAI") retains at least 20% and up to 100% of its biological activity (which can be assessed as potency or as toxicity by an in vivo $LD_{50}$ or $ED_{50}$ measure) in the presence of a compound which is stabilizing, stabilizes or which provides stabilization to the PAI. For example, upon (1) preparation of serial dilutions from a bulk or stock solution, or (2) upon reconstitution with saline or water of a lyophilized, or vacuum dried botulinum toxin containing pharmaceutical composition which has been stored at or below about −2 degrees C. for between six months and four years, or (3) for an aqueous solution botulinum toxin containing pharmaceutical composition which has been stored at between about 2 degrees and about 8 degrees C. for from six months to four years, the botulinum toxin present in the reconstituted or aqueous solution pharmaceutical composition has (in the presence of a compound which is stabilizing, stabilizes or which provides stabilization to the PAI) greater than about 20% and up to about 100% of the potency or toxicity that the biologically active botulinum toxin had prior to being incorporated into the pharmaceutical composition.

"Substantially free" means present at a level of less than one percent by weight of the pharmaceutical composition.

"Therapeutic formulation" means a formulation can be used to treat and thereby alleviate a disorder or a disease, such as a disorder or a disease characterized by hyperactivity (i.e. spasticity) of a peripheral muscle.

A pharmaceutical composition within the scope of my invention can comprise a Clostridial toxin, such as a botulinum toxin, and a polysaccharide as a primary stabilizer (as a protein stabilizer), and have a reduced toxicity.

The botulinum toxin can be present as a botulinum toxin complex (i.e. as an approximately 300 to about 900 kiloDalton complex depending upon the particular botulinum toxin serotype) or the botulinum toxin can be is present as a pure or purified botulinum toxin (i.e. as the botulinum toxin molecule of about 150 kiloDaltons). The pharmaceutical composition can also comprise a secondary stabilizer, such as a metal (i.e. zinc) or NAT.

Significantly, a pharmaceutical composition within the scope of my invention can have an enhanced potency or stability. By enhanced potency it is meant that the potency of a first botulinum toxin pharmaceutical composition is greater than the potency of a second botulinum toxin pharmaceutical composition.

Furthermore, a pharmaceutical composition within the scope of my invention can have an enhanced anti-microbial activity. By enhanced anti-microbial activity it is meant that the ability of a first botulinum toxin pharmaceutical composition with a particular component to inhibit the growth in a liquid solution of a particular microorganism is greater than the ability of a liquid solution of a second botulinum toxin pharmaceutical composition without the particular component present in the first botulinum toxin pharmaceutical composition to inhibit the growth of the same microorganism under the same conditions.

Another preferred embodiment of my invention is a pharmaceutical composition which can comprise (or which can consist essentially of or which can consist of) a botulinum toxin, a primary stabilizer, and a secondary stabilizer.

A pharmaceutical composition within the scope of the present invention can also include a neurotoxin, and a polysaccharide and have a reduced toxicity. The polysaccharide stabilizes the neurotoxin. The pharmaceutical compositions disclosed herein can have a pH of between about 5 and 7.3 when reconstituted or upon injection. The average molecular weight of a disaccharide unit of the polysaccharide is preferably between about 345 D and about 2,000 D. In a more preferred embodiment, the average molecular weight of a disaccharide unit of the polysaccharide is between about 350 kD and about 1,000 kD and in a most preferred embodiment between about 375 D and about 700 D. Additionally, the polysaccharide can comprise at least about 70% amylopectin. Furthermore, the weight average molecular weight of the polysaccharide itself is between about 20 kD and about 2,500 kD.

Preferably, substantially all of the disaccharide units of the polysaccharide comprise ether linked glucopyranose molecules. An average of about 4 to about 10 of the hydroxyl groups present on each 10 of the glucopyranoses present in the polysaccharide are substituted, through an ether linkage, with a compound of the formula $(CH_2)_n$—OH, where n can be an integer from 1 to 10. More preferably, n is an integer between 1 and 3.

In a particularly preferred embodiment, an average of about 6 to about 9 of the hydroxyl groups present on each 10 of the glucopyranoses present in the polysaccharide are substituted, through an ether linkage, with a compound of the formula $(CH_2)_n$—OH, where n can be an integer from 1 to 10. And in a most preferred embodiment, an average of about 7 to about 8 of the hydroxyl groups present on each 10 of the glucopyranoses present in the polysaccharide are substituted, through an ether linkage, with a compound of the formula $(CH_2)_n$—OH, where n can be an integer from 1 to 10.

A detailed embodiment of the present invention can be a pharmaceutical composition with a reduced toxicity and suitable for injection into a human patient, which includes a botulinum toxin, and a polysaccharide. The polysaccharide can comprise a plurality of linked glucopyranose units, each glucopyranose unit having a plurality of hydroxyl groups, wherein an average of about 6 to about 9 of the hydroxyl groups present on each 10 of the glucopyranoses present in the polysaccharide are substituted, through an ether linkage, with a compound of the formula $(CH_2)_n$—OH, where n can be an integer from 1 to 4. The polysaccharide can be an ethyl ether substituted polysaccharide.

The pharmaceutical composition is suitable for administration to a human patent to achieve a therapeutic effect, and the neurotoxin can be one of the botulinum toxin serotypes A, B, $C_1$, D, E, F and G. In a preferred embodiment of the present invention, the pharmaceutical composition comprises a botulinum toxin, and a hydroxyethyl starch.

Another embodiment of the present invention can encompass a pharmaceutical composition which includes a botulinum toxin, a polysaccharide, and an amino acid or a polyamino acid.

Whether the pharmaceutical composition comprises, beside the neurotoxin active ingredient, only a polysaccharide stabilizer, only an amino acid stabilizer or both polysaccharide and amino acid stabilizers, the pharmaceutical composition retains its potency substantially unchanged for six month, one year, two year, three year and/or four year periods when stored at a temperature between about $-1°$ C. and about $-15°$ C. Additionally, the indicated pharmaceutical compositions can have a potency or % recovery of between about 20% and about 100% upon reconstitution. Alternately or in addition, the pharmaceutical composition can have a potency of between about 10 U/mg and about 30 U/mg upon reconstitution, such as a potency of about 20 U/mg upon reconstitution. Significantly, the pharmaceutical composition is devoid of any albumin. Thus, the pharmaceutical composition can be substantially free of any non-toxin complex proteins. Notably, the amino acid can be present in an amount of between about 0.5 mg and about 1.5 mg of amino acid per 100 units of botulinum toxin.

The polysaccharide can be a starch such as a hydroxyethyl starch, which, when the pharmaceutical composition comprises about 100 units of the botulinum toxin, there can be between about 500 μg and about 700 μg of the hydroxyethyl starch present. Preferably, the botulinum toxin is botulinum toxin type A, and the amino acid, when present, is selected from the group consisting of lysine, glycine, histidine and arginine.

A further detailed embodiment of the present invention can be a stable, high potency, non-pyrogenic, vacuum dried botulinum toxin type A pharmaceutical composition, comprising a botulinum toxin type A complex, a polysaccharide, and, an amino acid or a polyamino acid. The pharmaceutical composition can be albumin free, have a 1 year shelf life at $-5$ C with about 90% potency immediately upon reconstitution with saline or water and about 80% potency 72 hours after reconstitution and storage at 2 C. Additionally, the pharmaceutical composition can have a specific toxicity of at least about $10^7$ U/mg upon reconstitution.

My invention also encompasses a botulinum toxin formulation which comprises a botulinum toxin hydroxyethyl starch (HES) glycine and providine.

The present invention also encompasses a lyophilized or vacuum dried pharmaceutical composition consisting essentially of a high molecular weight polysaccharide and a botulinum toxin, wherein the botulinum toxin is stabilized by the high molecular weight polysaccharide. The high molecule weight polysaccharide can be selected from the group consisting of hydroxymethyl starch, hydroxyethyl starch, hydroxypropyl starch, hydroxybutyl starch, and hydroxypentyl starch and The botulinum toxin can be selected from the group consisting of botulinum toxin types A, B, $C_1$, D, E, F and G.

The polysaccharide can be present in the pharmaceutical composition in an amount of between about $1 \times 10^{-9}$ moles of the polysaccharide per unit of a botulinum toxin to about $2 \times 10^{-12}$ moles of the polysaccharide per unit of the botulinum toxin.

The present invention also includes (a) a method for making a pharmaceutical composition, comprising the step of preparing a mixture of a botulinum toxin and a polysaccharide comprised of covalently linked repeating monomers, wherein the average monomer molecular weight is between about 350 D and about 1,000 D, and (b) a method for stabilizing a clostridial neurotoxin against denaturation or aggregation, the method comprising the step of contacting a clostridial neurotoxin with a stabilizing composition comprising a polysaccharide. The contacting step in this later method can comprise the step of adding to an aqueous solution or to a lyophilized or vacuum dried powder containing a clostridial neurotoxin an effective amount of the polysaccharide.

A further aspect of the present invention is a pharmaceutical composition, comprising a botulinum toxin, and a recombinantly made albumin. This composition preferably also includes an acetyltryptophanate and salts and derivatives thereof.

An additional embodiment of the present invention is a device for injecting a pharmaceutical composition comprising a dual chamber prefilled syringe, one chamber of which syringe contains a botulinum toxin and the second chamber of which syringe contains a diluent or buffer.

A further embodiment of the present invention is a method for using a pharmaceutical composition, the method comprising the step of local administration of the pharmaceutical composition to a patient to achieve a therapeutic effect, wherein the pharmaceutical composition comprises a botulinum toxin, a polysaccharide and an amino acid.

Significantly, my invention also includes a pharmaceutical composition, comprising a botulinum toxin, and an amino acid. My invention also includes a stable pharmaceutical composition, consisting essentially of a botulinum toxin, and an amino acid. These pharmaceutical compositions can be albumin free, polysaccharide free, has a 1 year shelf life at −5 C with at least about 90% potency upon reconstitution with saline or water and about 80% potency 72 hours after reconstitution and storage at 2 C.

In one aspect of the invention, a method for immobilizing a mammal comprises the step of administering a composition, which comprises at least one botulinum toxin serotype and a polysaccharide that stabilizes the botulinum toxin and is non-immunogenic to the mammal. In one embodiment, the foregoing method may be practiced by administering a composition comprising a hetastarch.

In another embodiment of the invention, a method for immobilizing a mammal, comprises the step of administering a composition to the mammal, wherein the composition comprises (i) at least one botulinum toxin serotype, and (ii) a polysaccharide, which comprises a plurality of linked glucopyranose units that each have a plurality of hydroxyl groups present on each of the glucopyranoses present in the polysaccharide are substituted, through an ether linkage, with a compound of the formula $(CH_2)_n$—OH, where n can be an integer from 1 to 4.

In another embodiment of the invention, a method for immobilizing a mammal comprises the step of administering a composition to the mammal, wherein the composition comprises a botulinum toxin, and a hydroxyethyl starch, thereby immobilizing the mammal.

The foregoing methods may be practiced utilizing a composition that comprises a botulinum toxin type A. In other embodiments of the invention, the foregoing methods may be practiced with a composition that comprises botulinum toxin type B. In further embodiments of the invention, the methods may be practiced with a composition that comprises a plurality of botulinum toxin serotypes, such as botulinum toxin serotypes selected from the group consisting of botulinum toxin serotypes A, B, $C_1$, D, E, F and G. In certain embodiments of the invention, purified botulinum toxins may be used. In other embodiments, modified botulinum toxins may be used. The compositions used in the foregoing methods may also include one or more amino acids in addition to the botulinum toxin and the polysaccharide.

In yet additional embodiments of the invention, the compositions used in the foregoing methods can be administered intramuscularly to the patient. In other embodiments, the compositions can be administered subcutaneously and/or intrathecally.

DESCRIPTION

The present invention is based upon the discovery that a Clostridial toxin pharmaceutical composition, with a stabilized Clostridial toxin, a reduced toxicity of the pharmaceutical composition and/or with a reduced antigenicity, as well as being free of animal derived proteins (such as a blood pooled or blood fraction derived human serum albumin or gelatin) can be made by using a polysaccharide as the primary or protein stabilizer of the Clostridial toxin.

The present invention also encompasses a stable Clostridial toxin containing pharmaceutical composition formulated free of any animal derived protein or donor pool albumin by incorporating both an polysaccharide and an amino acid into the pharmaceutical composition. In particular, the present invention encompasses a stable botulinum toxin containing pharmaceutical composition suitable for administration to a patient for therapeutic effects made by replacing the donor pool albumin present in known botulinum toxin containing pharmaceutical compositions with a high molecular weight polysaccharide derived from starch and/or with certain reactive amino acids.

Polysaccharide Containing Pharmaceutical Composition

I have discovered that a suitable replacement for albumin in a Clostridial toxin pharmaceutical composition can be a compound which is neither another protein, nor a low molecular weight, non-protein compound. Thus, I have discovered that particular high molecular weight polysaccharides can function as neurotoxin stabilizers in a pharmaceutical composition. As set forth below, an amino acid can also, or in the alternative, be added to the pharmaceutical composition to increase the stability and useful storage life of the pharmaceutical composition.

The polysaccharide used in the present invention can impart stability to a neurotoxin active ingredient, such as a botulinum toxin, present in the pharmaceutical composition by: (1) reducing adhesion (commonly referred to as "stickiness") of the botulinum toxin to surfaces, such as the surfaces of laboratory glassware, vessels, the vial in which the pharmaceutical composition is reconstituted and the inside surface of the syringe used to inject the pharmaceutical composition. Adhesion of the botulinum toxin to surfaces can lead to loss of botulinum toxin and to denaturation of retained botulinum toxin, both of which reduce the toxicity of the botulinum toxin present in the pharmaceutical composition. (2) reducing the denaturation of the botulinum toxin and/or dissociation of the botulinum toxin from other non-toxin proteins present in the botulinum toxin complex, which denaturation and/or dissociation activities can occur because of the low dilution of the botulinum toxin present in the pharmaceutical composition (i.e. prior to lyophilization or vacuum drying) and in the reconstituted pharmaceutical composition. (3) reducing loss of botulinum toxin (i.e. due to denaturation or dissociation from non-toxin proteins in the complex) during the considerable pH and concentration changes which take place during preparation, processing and reconstitution of the pharmaceutical composition.

The three types of botulinum toxin stabilizations provided by the polysaccharide conserve and preserve the botulinum toxin with it native toxicity prior to injection of the pharmaceutical composition.

In certain embodiments of the invention, the pharmaceutical compositions of the invention may comprise a plurality of botulinum toxin serotypes. In other words, the composition may include two or more different botulinum toxin serotypes. For example, a composition may include botulinum toxin serotypes A and B. In another embodiment, a composition may include botulinum toxin serotypes A and E. Using a combination of botulinum toxin serotypes will permit caregivers to customize the composition to achieve a desired effect based on the condition being treated. In an additional embodiment of the invention, the composition may comprise a modified botulinum toxin. The modified botulinum toxin will preferably inhibit the release of neurotransmitter from a neuron, but may have a greater or lower potency than the native botulinum toxin, or may have a greater or lower biological effect than the native botulinum toxin. Because the compositions of the invention may be used for relatively long-term treatment of animals, the compositions may be provided in a relatively pure form. In one embodiment, the compositions are of a pharmaceutical grade. In certain embodiments, the clostridial neurotoxin has a greater than 95% purity. In additional embodiments, the clostridial neurotoxin has a purity greater than 99%.

A preferred polysaccharide for use in the present composition comprises a plurality of glucose monomers (mol wt 180) with one or more substituents on a majority of the glucose monomers, so that the preferred polysaccharide has a molecular weight range of between about 20 kD and about 800 kD. Surprisingly, such a polysaccharide can stabilize a neurotoxin component present in a pharmaceutical composition. The present invention excludes from its scope disaccharide oligosaccharides with a weight average molecular weight of less than about 20 kD. The present invention also excludes from its scope cyclic polymers such as the cyclodextrins. The latter two classes of compounds are excluded from the scope of the present invention because the desired stabilization characteristics of the preferred polysaccharide while requiring a relatively high molecular compound (i.e. molecular weight in excess of 20 kD) do not require and indeed can make no use of the small lipophilic cavity characteristic of the cyclodextrins, because the cyclodextrin lipophilic cavity is much smaller in size than the size of the neurotoxins stabilized by the preferred polysaccharides of the present invention. Additionally, the cyclodextrins are low molecular weight compounds comprising only about 6 to 8 glucose monomers.

The present invention also encompasses a method for stabilizing pharmaceutical compositions which contain a clostridial toxin with a polysaccharide. The stabilizing effect is achieved by bringing a clostridial toxin in contact with the polysaccharide. Examples of suitable polysaccharides within the scope of my invention include certain starch and starch derivatives. As noted, the polysaccharide exhibits a stabilizing effect on the clostridial toxin. Furthermore, the effect of the polysaccharide to stabilize a clostridial toxin can be enhanced by the addition of an amino acid.

Unexpectedly, I have discovered that 2-hydroxyethyl starch demonstrates a unique ability to stabilize the botulinum toxin present in a botulinum toxin containing pharmaceutical composition, thereby providing a pharmaceutical composition which is devoid of the potential for harboring a transmissible disease derived from human blood or blood fraction donor pools or animal derived proteins like gelatin.

Thus, I have discovered that the particular high molecular weight polysaccharide, hydroxyethyl starch, can stabilize the toxin during formulation, drying, storage and reconstitution. Preferably, to further stabilize the protein active ingredient, an amino acid is also included in the polysaccharide containing formulation.

The polysaccharide in the pharmaceutical composition is preferably admixed with the clostridial neurotoxin in an amount of about 1 µg of polysaccharide per unit of botulinum toxin to about 10 µg of polysaccharide per unit of botulinum toxin. More preferably the polysaccharide in the pharmaceutical composition is admixed with the clostridial neurotoxin in an amount of about 4 µg of polysaccharide per unit of botulinum toxin to about 8 µg of polysaccharide per unit of botulinum toxin. In a most preferred embodiment, where the polysaccharide is a hydroxyethyl starch, the hydroxyethyl starch in the pharmaceutical composition is preferably admixed with a botulinum toxin type A complex in an amount of about 5 µg of hydroxyethyl starch per unit of botulinum toxin to about 7 µg of hydroxyethyl starch per unit of botulinum toxin. Most preferably, the hydroxyethyl starch in the pharmaceutical composition is admixed with a botulinum toxin type A complex in an amount of about 6 µg of hydroxyethyl starch per unit of botulinum toxin. Since BOTOX® contains about 100 units of botulinum toxin type A complex per vial and the average molecular weight of hydroxyethyl starch is generally regarded as being between about 20 kD and about 2,500 kD, the most preferred concentration of hydroxyethyl starch is between about $1\times10^{-9}$ moles per unit of botulinum toxin (M/U) to about $2\times10^{-12}$ moles per unit of botulinum toxin. In another preferred embodiment, for a 100 U botulinum toxin type A complex pharmaceutical composition, about 600 µg of the hydroxyethyl starch and about 1 mg of an amino acid, such as lysine, glycine, histidine or arginine is included in the formulation. Thus, my invention encompasses use of both a polysaccharide and an amino acid, or a polyamino acid to stabilize the neurotoxin active ingredient in the pharmaceutical composition.

Additionally, my invention also encompasses use of a suitable amino acid in a sufficient amount to stabilize the protein active ingredient in a pharmaceutical composition, either in the presence of or to the exclusion of any polysaccharide being present in the formulation. Thus, I have surprisingly discovered that the inclusion of certain amino acids into a neurotoxin containing, pharmaceutical composition formulation can extend the useful shelf life of such a pharmaceutical composition. Thus, my invention encompasses a neurotoxin containing pharmaceutical composition which includes an amino acid and the use of such a pharmaceutical composition. Without wishing to be bound by theory, I can postulate that since a neurotoxin, such as a botulinum toxin, is susceptible to oxidation, due to the presence of disulfide linkages in the toxin complex, the inclusion of an oxidizable amino acid may act to reduce the probability that oxidizers, such as peroxides and free radicals, will react with the neurotoxin. Thus, the likelihood that the oxidizable neurotoxin disulfide linkage will be oxidized by an oxidizer, such as peroxides and free radicals, can be reduced upon inclusion of an amino acid which can act as an oxidative sink, that is as a scavenger for oxidizing compounds. A suitable amino acid is an amino acid which is subject to oxidation. Examples of preferred amino acids are methionine, cysteine, tryptophan and tyrosine. A particularly preferred amino acid is methionine.

A preferred embodiment of my invention can also include the use of two or more amino acids either alone or in combination with a polysaccharide to stabilize the protein active ingredient in a pharmaceutical composition. Thus, for a 100 U botulinum toxin type A containing pharmaceutical composition, about 0.5 mg of lysine and about 0.5 mg of glycine can be used, either with or without between about 500 µg and about 700 µg of hetastarch.

Thus, as set forth above, my invention encompasses a protein containing, pharmaceutical composition which includes a polysaccharide. The polysaccharide acts to stabilize the protein active ingredient in the pharmaceutical composition. Additionally, my invention also includes a protein containing, pharmaceutical composition which includes a polysaccharide and an amino acid. Surprisingly, I have discovered that the inclusion of certain amino acids into a neurotoxin containing, pharmaceutical composition formulation which includes a carbohydrate can extend the useful shelf life of such a pharmaceutical composition. Thus, my invention encompasses a neurotoxin containing pharmaceutical composition which includes both a polysaccharide and an amino acid and the use of such a pharmaceutical composition. Furthermore, my invention also encompasses use of an amino acid without any polysaccharide being present in the protein active ingredient pharmaceutical composition.

It is known that protein containing pharmaceutical compositions which also contain sugars, polysaccharides and/or carbohydrates (referred to hereafter as "reactive compounds") are inherently unstable due to the fact that a protein and one of the three indicated reactive compounds can undergo the well-described Maillard reaction. Extensive, largely fruitless, research has been carried out to try and reduce the incidence or prevalence of this (for example) protein-polysaccharide Maillard reaction, by reduction of moisture or by the use of non-reducing sugars in the formulation. My discovery is based upon the observation that inclusion of a high concentration of a highly reactive amino acid encourages the Maillard reaction to take place between the stabilizing polysaccharide and the added amino acid. By providing an abundant amine source for the carbohydrate to react with, the probability of the protein drug (i.e. botulinum toxin active ingredient) becoming involved in the Maillard is reduced, thereby reducing this degradation pathway of the protein active ingredient and in this manner thereby stabilizing the protein active ingredient in the pharmaceutical composition.

Preferably, any compound containing a primary or secondary amine can be used for this purpose. Most preferred are amino acids, such as lysine, glycine, arginine. Polyamino acids, such as polylysine are also suitable. Cationic amino acids such as lysine may undergo ionic attraction, binding acidic proteins (e.g., botulinum toxins) and shield the active protein from contact with sugars. Polylysine, in addition to being larger and therefore more likely to act as a shield, provides the additional advantage of being antibacterial.

Another aspect of my invention is to pre-react the sugar and amino acid components to exhaust Maillard reaction potential before adding the active protein component (botulinum toxin) to the sugar and amino acid formulation ingredients, thereby substantially limiting the active protein's exposure to Maillard reactions.

Thus, my invention encompasses a pharmaceutical composition containing and the use of an amino acids and polyamino acids as Maillard reaction inhibitors in protein (i.e. botulinum toxin) drug formulations which contain starches, sugars and/or polysaccharides.

The invention embodies formulations of active proteins (e.g., botulinum toxin) in combination with a stabilizing starch, sugar, or polysaccharide or combination of these, and an amino acid such as lysine.

Significantly, I have discovered that hydroxyethyl starch does not undergo or undergoes a much attenuated rate or level of Maillard reactions with a protein, such as a botulinum toxin, when hydroxyethyl starch is compared to other polysaccharides or carbohydrates. Additionally, I have discovered that inclusion of an amino acid enhances the preservation effect of hydroxyethyl starch, possibly by acting as a competitive inhibitor, that is by competing with the toxin for Maillard reaction reactive sugars. For this purpose, amino acids such as lysine, glycine, arginine and histidine are preferred amino acids. Polyamino acids, such as polylysine, which exhibit the desired competitive inhibition behavior can also be used. Notably, the specified amino and poly amino acids can also exhibit antimicrobial properties, providing therefore the added benefit of reducing bacterial contamination in the pharmaceutical composition.

Reducing sugars, such as glucose and glucose polymers, undergo Maillard reaction with proteins. Even sugar alcohols like mannitol can react, albeit sometimes through contaminants or degradation products. Therefore a polysaccharide can stabilize the toxin for a period of time only to chemically react later, thereby causing reduced storage stability. It is obvious that the choice of polysaccharide is critical. I have discovered that the rate of hydroxyethyl starch participation in the Maillard reaction is very low. Additionally, I have found that hydroxyethyl cellulose, although structurally very similar to hydroxyethyl starch, is unsuitable to use as a stabilizer, since I have found that hydroxyethyl cellulose can rapidly react in a model system with lysine. This not only means that hydroxyethyl starch has an obvious advantage over other sugar (i.e. polysaccharide) stabilizers, but that even excipients similar to hydroxyethyl starch, such as hydroxyethyl cellulose, can be unsuitable to use as stabilizers of a protein active ingredient in a pharmaceutical formulation.

As noted, hydroxyethyl starch, can participate to at least some extent, in Maillard reactions. Thus, and as set forth above, a polysaccharide alone may not be sufficient to provide optimal stabilization of the toxin. Thus, I discovered the advantages of inclusion of an amino acid to act as a competitive inhibitor. Without wishing to be bound by theory, the hypothesis is that by providing another amine source, in high concentrations compared to the toxin, the probability of the Maillard reaction occurring with the toxin is reduced, thereby stabilizing the toxin. Any amino acid can be used however lysine being highly reactive and is a preferred amino acid.

Significantly, I have discovered that a botulinum toxin pharmaceutical composition formulated with hetastarch has a reduced toxicity, as well as a reduced antigenicity. It can be hypothesized that the reduced toxicity of the hetastarch botulinum toxin formulation upon either intramuscular or intravenous administration of amounts of botulinum toxin which are toxic when the botulinum toxin is formulated with a human serum albumin, is due to hetastarch mediated sequestration of the botulinum toxin by local and regional macrophages and monocytes of the reticuloendothelial system, where presumably the toxin undergoes lysosomal proteolysis. Thus, it is known that upon intravenous administration of hetastarch as a plasma expander, the hetastarch can be taken up by macrophages and retained for prolonged periods in the liver, lung, spleen and skin. See e.g. Sirtl, C., et al., *Tissue deposits of hydroxyethyl starch (HES): dose-dependent and time-related*, Br J Anaesth. 1999 April; 82(4):510-5; Reimann S., et al., [*Hydroxyethyl starch accumulation in the skin with special reference to hydroxyethyl starch-associated pruritus*]; Dtsch Med Wochenschr. 2000 Mar. 10; 125(10):280-5; Parth E., et al., *Histological and immunohistochemical investigations of hydroxyethyl-starch deposits in rat tissues*, Eur Surg Res. 1992;24(1):13-21; Jurecka W., et al., *Hydroxyethyl-starch deposits in human skin—a model for pruritus?*, Arch Dermatol Res. 1993;285(1-2):13-9

Thus, I have discovered that a botulinum toxin formulated with hetastarch not only retains the therapeutic paralytic activity of the toxin at the injection site upon intramuscular or subcutaneous of administration of the formulation (i.e. the hetastarch present in the formulation does not interfere with the activity of the botulinum toxin at the neuromuscular junction) but that the hetastarch formulation also has a markedly reduced toxicity.

My invention also encompasses addition of a preservative, either in the diluent or formulation itself, to allow extended storage. A preferred preservative is preserved saline containing benzyl alcohol.

A liquid formulation can be advantageous. A single-step presentation (e.g., pre-filled syringe) or a product configuration that the user perceives as a single-step presentation (e.g., dual-chambered syringe) would provide convenience by eliminating the reconstitution step. Freeze-drying is a complicated, expensive and difficult process. Liquid formulations are often easier and cheaper to produce. On the other hand liquid formulations are dynamic systems and therefore more susceptible to excipient interaction, fast reactions, bacterial growth, and oxidation than freeze-dried formulations. A compatible preservative might be needed. Anti-oxidants such as methionine might also be useful as scavengers especially if surfactants are used to reduce adsorption as many of these compounds contain or produce peroxides. Any of the stabilizing excipients which can be used in a freeze-dried formulation (e.g., hydroxyethyl starch or an amino acid such, lysine) might be adapted to use in a liquid formulation to assist in reducing adsorption and stabilize the toxin. Suspensions similar to those developed for insulin are also good candidates. Additionally, stabilizing botulinum toxin in a liquid vehicle might require a low pH vehicle as the toxin is reported to be labile above pH 7. This acidity could produce burning and stinging upon injection. A binary syringe could be employed. Inclusion of a co-dispensed buffer, sufficient to raise the pH to physiologic levels, would alleviate injection discomfort of a low pH while maintaining the toxin at a low pH during storage. Another dual-chambered syringe option would include diluent and lyophilized material segregated in separate chamber, only mixing upon use. This option provides the advantages of a liquid formulation without the additional resources and time.

Thus, the botulinum toxin can be prepared at low pH to be co-dispensed with a buffer which raises the pH to at or near physiological pH at the time of administration. The two chamber or binary syringe can have in the first chamber (next to the plunger) a liquid formulation of a botulinum toxin with a pH between 3 to 6 (i.e. at pH 4.0). The second chamber (next to the needle tip) can contain a suitable buffer, such as phosphate buffered saline at a higher pH (i.e. pH 7.0). Alternately, the first chamber can contain a saline diluent and the second chamber can contain a freeze dried or lyophilized neurotoxin formulation. The two chambers can be joined in such a way and the buffering components selected in such a way that the solutions mix at or near the needle, thereby delivering the final solution at a physiological pH. Suitable two chamber syringes to use as pre-filled syringes for the purposes set forth herein can be obtained from Vetter Pharma-Fertigung of Yardley, Pa.

There are distinct advantages to formulating botulinum toxin at a low pH. The toxin has a low isoelectric point (pI) and formulating proteins near their pI is a known way to stabilize a protein. Additionally, the toxin is used at a very low concentration making surface adsorption a problem. Use of a low pH solution can suppress ionization of toxin sites likely to interact with surfaces. The syringe and plunger materials are materials which reduce surface adsorption by the toxin. Suitable such materials are polypropylene.

As discussed herein, the neurotoxin may be prepared and purified using techniques well-known in the art. The purified toxin may subsequently be diluted in a stabilizer such as a polysaccharide (e.g., hetastarch), or a recombinant serum albumin, or a serum albumin of the species of animal receiving the neurotoxin. It is preferred that the stabilizer prevents or reduces denaturation of the toxin, and produces no, or minimal, immunogenic responses in the animal that will receive the toxin. Aliquots of the diluted toxin are then lyophilized using conventional procedures.

The lyophilized neurotoxin may be reconstituted before administering the neurotoxin to a subject by adding water, saline, or any buffer solution to the lyophilized neurotoxin. In certain embodiments, sodium free buffers may be preferred to help reduce denaturation of the neurotoxin.

The pharmaceutical compositions of the invention can be administered using conventional modes of administration. In preferred embodiments of the invention, the compositions are administered intramuscularly or subcutaneously to the subject. In other embodiments, the compositions of the invention may be administered intrathecally. In addition, the compositions of the invention may be administered with one or more analgesic or anesthetic agents.

The most effective mode of administration and dosage regimen for the compositions of this invention depends upon the type, severity, and course of the condition being treated, the animal's health and response to treatment, and the judgment of the treating doctor. Accordingly, the methods and dosages of the compositions should be tailored to the individual subject.

By way of example, and not by way of limitation, it may be preferred to administer the composition of the invention intramuscularly to reduce a muscle spasm.

My invention also encompasses a pharmaceutical composition comprising a botulinum toxin and a collagen for use to treat a variety of conditions wherein the botulinum toxin acts to paralyze a muscle and the collagen acts to provide a dermal filler.

As indicated above, dosages of the neurotoxin, such as botulinum toxin, in the compositions may vary. In one embodiment, the compositions contain a therapeutically effective amount of neurotoxin, for example, between about 1 U and about 500 U of botulinum toxin type A. Preferably the amounts are between about 10 U and about 300 U. More preferably the amount is between about 20 U and 250 U, such about 50 U to 200 U, or 70 U.

Alternatively, botulinum toxin, such as botulinum toxin type A, can be administered in amounts between about $10^{-3}$ U/kg and about 60 U/kg to alleviate pain experienced by a mammal. Preferably, the botulinum toxin used is administered in an amount of between about $10^{-2}$ U/kg and about 50 U/kg. More preferably, the botulinum toxin is administered in an amount of between about $10^{-1}$ U/kg and about 40 U/kg. Most preferably, the botulinum toxin is administered in an amount of between about 1 U/kg and about 30 U/kg. In a particularly preferred embodiment of the present disclosed methods, the botulinum toxin is administered in an amount of between about 1 U/kg and about 20 U/kg.

Compositions containing other serotypes of botulinum toxin may contain different dosages of the botulinum toxin. For example, botulinum toxin type B may be provided in a composition at a greater dose than a composition containing botulinum toxin type A. In one embodiment of the invention, botulinum toxin type B may be administered in an amount between about 1 U/kg and 150 U/kg. Botulinum toxin type B may also be administered in amounts of up to 20,000 U (mouse units, as described above). In another embodiment of the invention, botulinum toxin types E or F may be administered at concentrations between about 0.1 U/kg and 150 U/kg. In addition, in compositions containing more than one type of botulinum toxin, each type of botulinum toxin can be provided in a relatively smaller dose than the dose typically used for a single botulinum toxin serotype. The combination of botulinum toxin serotypes may then provide a suitable degree and duration of paralysis without an increase in diffusion of the neurotoxins (e.g. see U.S. Pat. No. 6,087,327).

EXAMPLES

The following examples set forth specific embodiments of the present invention and are not intended to limit the scope of the invention.

Example 1

Preparation and Potency of a Botulinum Toxin Pharmaceutical Composition Containing Human Serum Albumin (Prior Art)

Formulation I

A botulinum toxin type A complex was obtained from a culture of the Hall strain of *Clostridium botulinum* grown in a medium containing N-Z amine and yeast extract. The botulinum toxin type A complex was purified from the culture solution by a series of acid precipitations to a crystalline complex consisting of the active high molecular weight toxin protein and an associated hemagglutinin protein. The crystalline complex was then re-dissolved in a solution containing saline and albumin and sterile filtered (0.2 microns) prior to vacuum-drying. The vacuum dried composition was reconstituted with sterile, non-preserved saline prior to injection. Each vial of vacuum dried composition contains about 100 units (U) of *Clostridium botulinum* toxin type A complex, 0.5 milligrams of human serum albumin and 0.9 milligrams of sodium chloride in a sterile, vacuum-dried form without a preservative. This pharmaceutical composition is Formulation I, sold commercially under the trade name BOTOX® in 100 unit vials and is known to have an unchanged potency, after storage at −5 degrees Celsius for six months or longer followed by reconstitution in saline, of about 100 units.

Example 2

Preparation and Potency of a Botulinum Toxin Pharmaceutical Composition Containing 2-Hydroxyethyl Starch Formulation II Botulinum toxin type A purified neurotoxin complex pharmaceutical formulations were prepared in the same manner set forth in Example 1 above, except that the 0.5 milligrams of albumin in Example 1 was replaced by either 500 μg or 600 μg of hetastarch. This pharmaceutical composition is Formulation II (albumin free). It was determined that full potency was maintained upon preparation of the hetastarch containing formulations. Thus, Formulation II, with either 500 or 600 ug of hetastarch, had a potency as measured at the time of reconstitution of the lyophilized, 100 U (±20 U) botulinum toxin type A Formulation II of from 96 to 128 units. Three separate Formulation II batches had potency measurements at the time of reconstitution of, respectively, 105, 111 and 128 units. Potency was measured using the standard mouse $LD_{50}$ assay.

Example 3

Preparation and Potency of Botulinum Toxin Pharmaceutical Composition Containing Hydroxyethyl Starch and Glycine Formulation IIA Formulation IIA was made by adding 1 mg glycine USP, and 0.004 mg zinc chloride USP to the Formulation II of Example 2, reconstituted with sodium chloride and it's potency was determined ($T_0$ potency) using the mouse $LD_{50}$ assay. Lyophilized (i.e. not reconstituted) Formulation IIA was then stored for seven months at −5° C. At the end of this seven month period the potency of Formulation IIA was again determined upon reconstitution in sodium chloride, using the mouse $LD_{50}$ assay, to be essentially unchanged (i.e. potency differed by less than 5% from the $T_0$ potency).

Example 4

Toxicity of a Botulinum Toxin Pharmaceutical Composition Containing Human Serum Albumin Upon Intramuscular Administration Formulation I An experiment was carried out to evaluate the toxicity of a botulinum toxin pharmaceutical composition containing human serum albumin (i.e. BOTOX®) upon intramuscular administration.

Formulation I was prepared as in Example 1 (i.e. 100 units botulinum toxin type A complex, 0.5 mg human serum albumin USP, 0.9 mg sodium chloride USP, vacuum dried, without a preservative). The vacuum dried formulation was removed from the freezer, reconstituted with sodium chloride and administered within four hours.

A Formulation I placebo containing 0.5 mg human serum albumin USP and 0.9 mg sodium chloride USP was also prepared. The diluent used for both formulation and placebo was 0.9% sodium chloride inj. USP.

Six separate lots of twelve Sprague Dawley albino rats (n=12, 6 male, 6 female; 72 study rats plus 12 control rats for placebo injection], about 10 weeks old, Charles River Labs, Hollister, Calif.) were injected with single intramuscular injections into the left gastrocnemius muscle of the left hind limb of Formulation I at doses of 5, 10, 50, 100, 200 or 300 units/kg, respectively. A control group (n=12; 6 male, 6 female) was injected with single intramuscular injections of the vehicle (serum human and sodium chloride) at the equivalent dose volume (0.2 ml/kg). Rats were sacrificed and necropsied 14 days after the single injection. The parameters evaluated were mortality and morbundity, clinical observations, body weight, injected and non-injected gastrocnemius muscle weight, macroscopic observations and microscopic pathology of the injected and non-injected gastrocnemius and biceps femoris muscles.

It was determined that intramuscular administration of Formulation I induced in rats local pharmacological effects (i.e. curling of the left hind toes, limping, left abdominal distension, small left hind limb calf muscles) at doses of 5 units/kg or higher, and clinical signs of toxicity (i.e. chromodacryorrhea, chromorhinorrhea, piloerrection, hunched posture, soiled perianal region, immobility and morbundity) at doses of 50 units/kg or higher. 50% of the rats died at the 100 units/kg dose level and 100% of the rats died at the 200 and 300 units/kg dose levels.

This experiment determined that Formulation I (a botulinum toxin pharmaceutical composition containing human serum albumin) can be lethal upon intramuscular administration to rats at a 100 unit/kg dose level.

Example 5

Reduced Toxicity of a Botulinum Toxin Pharmaceutical Composition Containing Hydroxyethyl Starch Upon Intramuscular Administration Formulation II An experiment was carried out to evaluate the toxicity of a botulinum toxin pharmaceutical composition containing 2-hydroxyethyl starch (Formulation II) upon intramuscular administration.

Formulation II was prepared as in Example 2 (i.e. 100 units botulinum toxin type A complex, 0.6 mg hetastarch and 0.9 mg NaCl). The vacuum dried formulation was removed from the freezer, reconstituted with sodium chloride and administered within four hours.

A Formulation II placebo containing 0.6 mg hetastarch was also prepared. The diluent used for both formulation and placebo was 0.9% sodium chloride inj. USP.

Four separate lots of 8 Sprague Dawley rats (n=8; 4 male, 4 female) (40 rats total [including controls], 7-10 weeks old, Charles River Labs, Hollister, Calif.) were given single intramuscular injections into the left gastrocnemius muscle of the left hind limb of Formulation II at doses of 10, 50, 100 and 200 units/kg. A control group (n=8; 4 male, 4 female) were injected with single intramuscular injections of the vehicle (serum human and sodium chloride) at the equivalent dose volume (0.2 mL/kg). Rats were sacrificed and necropsied 14 days after the single injection. The parameters evaluated were mortality, clinical observations, body weight, injected and non-injected gastrocnemius muscle weight, macroscopic observations.

Surprisingly no mortality was observed any dose level in any of the drug injected rats. Local pharmacological effects (curling of the left hind toes, limping, decreased injected muscle weight) were observed in the drug treated groups. Drug related clinical findings indicative of toxicity included one incidence each of chromodacryorrhea and chromorrhinorrhea in one male rat in the 200 U/kg dose group.

As set forth in Example 4, intramuscular Formulation I induced in rats local pharmacological effects at doses of 5 units/kg or higher, clinical signs of toxicity at doses of 50 units/kg or higher and death at doses of 100 units/kg or higher. However the experiment carried out in this example showed that intramuscular doses of Formulation II as high as 200 units/kg induced only local pharmacological effects (i.e. curling of the left hind toes, limping, palpably smaller left calf muscles and decreased injected muscle weight), with minimal clinical signs of toxicity and no mortality.

Hence, it can be concluded that Formulation II showed significantly less toxicity and similar local pharmacological effects, as compared to Formulation I.

Example 6

Reduced Toxicity of a Botulinum Toxin Pharmaceutical Composition Containing Hydroxyethyl Starch and Glycine Upon Intramuscular Administration Formulation IIA An experiment was carried out to evaluate the toxicity of a botulinum toxin pharmaceutical composition containing 2-hydroxyethyl starch and glycine upon intramuscular administration.

Formulation IIA was prepared as in Example 3 (i.e. 100 units botulinum toxin type A complex, 0.6 mg hetastarch and 0.9 mg NaCl) and 1 mg glycine USP, but no zinc chloride, was added to make the formulation. The vacuum dried formulation was removed from the freezer, reconstituted with sodium chloride and administered within four hours.

A Formulation IIA placebo containing 0.6 mg hetastarch and 1 mg glycine was also prepared. The diluent used for both formulation and placebo was 0.9% sodium chloride inj. USP.

Two separate lots of 5 female Sprague Dawley rats (n=5, all female) (15 rats total [including controls], 7-10 weeks old, Charles River Labs, Hollister, Calif.) were given single intramuscular injections into the left gastrocnemius muscle of the left hind limb of Formulation II at doses of either 100 or 200 units/kg. A control group (n=5; all female) were injected with single intramuscular injections of the vehicle (hetastarch with glycine in sodium chloride diluent) at the equivalent dose volume (0.2 mL/kg). Rats were sacrificed and necropsied 14 days after the single injection. The parameters evaluated were mortality and morbundity, clinical observations, body weight, injected and non-injected gastrocnemius muscle weight, macroscopic observations and microscopic pathology of the injected and non-injected gastrocnemius and biceps femoris muscles.

Surprisingly no mortality was observed at any dose level in any of the drug injected rats. Nor were there observed any drug related clinical signs of toxicity at any dose level in any of the rats. Local pharmacological effects (curling of the left hind toes, limping, palpably smaller left calf muscles and decreased injected muscle weight) were observed in the drug treated groups.

As set forth in Example 4, intramuscular Formulation I induced in rats local pharmacological effects at doses of 5 units/kg or higher, clinical signs of toxicity at doses of 50 units/kg or higher and death at doses of 100 units/kg or higher. However the experiment carried out in this example showed that intramuscular doses of Formulation IIA as high as 200 units/kg induced only local pharmacological effects, with no clinical signs of toxicity or mortality. Hence, it can be concluded that a botulinum toxin pharmaceutical composition containing 2-hydroxyethyl starch (with or without glycine) has upon intramuscular administration a significantly lower toxicity than does a botulinum toxin pharmaceutical composition containing human serum albumin.

Since both Formulations II and IIA showed reduced toxicity (as compared to Formulation I), but glycine was not present in Formulation II, therefore the reduced toxicity of Formulations II and IIA was due to the presence of the hydroxyethyl starch present, and was not due to any effect of the glycine.

Example 7

Comparison of Toxicity of Botulinum Toxin Pharmaceutical Compositions Containing Human Serum Albumin or Hydroxyethyl Starch Upon Intravenous Administration Formulations I and IIA An experiment was carried out to evaluate the toxicity of a botulinum toxin pharmaceutical composition containing 2-hydroxyethyl starch upon intravenous administration of the pharmaceutical composition. It was expected that an intravenously administered botulinum toxin pharmaceutical composition would result in widespread systemic effects, including muscle weakness, systemic toxicity, respiratory failure and subject mortality.

Formulation I was prepared as set forth in Example 1 (i.e. 100 units botulinum toxin type A complex, 0.5 mg human serum albumin ("HSA") USP, 0.9 mg sodium chloride USP). The vacuum dried formulation was removed from the freezer, reconstituted with sodium chloride and administered within four hours.

Formulation IIA was prepared as in Example 3 (i.e. 100 units botulinum toxin type A complex, 0.6 mg hetastarch and 0.9 mg NaCl) and 1 mg glycine USP, and 0.004 mg zinc chloride USP was added to the formulation. The vacuum dried formulation was removed from the freezer, reconstituted with sodium chloride and administered within four hours.

A Formulation I placebo containing 0.5 mg human serum albumin USP and 0.9 mg sodium chloride USP was also prepared. A Formulation IIA placebo containing 0.6 mg hetastarch, 1 mg glycine USP, and 0.004 mg zinc chloride USP was also prepared.

The diluent used for both formulations and placebos was 0.9% sodium chloride inj. USP.

Separate lots of 60 male and 60 female Sprague Dawley rats (n=12; six male, six female) (120 rats total, 6-10 weeks old, Charles River Labs, Hollister, Calif.) were injected with single intravenous injections of the two botulinum toxin formulations into the lateral tail vein at 10 units per kg of animal weight, 50 units per kg, 100 units per kg or 200 units per kg dose levels of the botulinum toxin type A. Two separate control groups (n=12; six male, six female) were injected with single intravenous injections of each of the two different placebos at an equivalent dose volume (0.2 ml/kg).

Surviving rats were sacrificed and necropsied 14 days after the single injection. The parameters evaluated were mortality, clinical observations, body weight and macroscopic observations.

The results of this experiment are shown by Table 1. Not unexpectedly, mortality occurred in all rats treated with ≧100 U/kg of any of the Formulation I. Surprisingly, no mortality was observed in any of the rats treated with Formulation IIA, at doses as high as 200 U/kg. Thus Formulation IIA exhibited a significantly lower systemic toxicity as compared to Formulation I.

TABLE 1

Toxicity of a Botulinum Toxin Hetastarch Formulation Compared to a Botulinum Toxin Human Serum Albumin Formulation Upon Intravenous Administration

| Group No. | Toxin Dose (U/kg) | Formulation or Placebo | Total No Dead/No. Dosed | Percent Mortality |
|---|---|---|---|---|
| 1 | 0 | Placebo HSA | 0/12 | 0 |
| 2 | 10 | I | 0/12 | 0 |
| 3 | 50 | I | 0/12 | 0 |
| 4 | 100 | I | 12/12 | 100 |
| 5 | 200 | I | 12/12 | 100 |
| 6 | 0 | Placebo Hetastarch | 0/12 | 0 |
| 7 | 10 | IIA | 0/12 | 0 |
| 8 | 50 | IIA | 0/12 | 0 |
| 9 | 100 | IIA | 0/12 | 0 |
| 10 | 200 | IIA | 0/12 | 0 |

Example 8

Botulinum Toxin Pharmaceutical Composition Containing Lysine

Formulation IIC

100 U botulinum toxin type A purified neurotoxin complex pharmaceutical formulations are prepared in the same manner set forth in Example 1 above, except that the 0.5 milligrams of albumin was replaced by 600 µg of hetastarch. In addition 1 mg of lysine is added to the formulation. A lyophilized, hetastarch plus lysine, albumin-free, 100 U *botulinum* toxin type A complex, pharmaceutical composition is then stored for one year at −5° C. At the end of this one year period the potency of this hetastarch plus lysine, toxin formulation is determined, using the mouse administration assay, to be essentially unchanged (i.e. potency differs by less than 5% from the original potency).

Example 9

Botulinum Toxin Pharmaceutical Composition Containing Histidine

Formulation IID

100 U botulinum toxin type A purified neurotoxin complex pharmaceutical formulations are prepared in the same manner set forth in Example 1 above, except that the 0.5 milligrams of albumin was replaced by 600 µg of hetastarch. In addition 1 mg of histidine is added to the formulation. A lyophilized, hetastarch plus histidine, albumin-free, 100 U botulinum toxin type A complex, pharmaceutical composition is then stored for one year at −5° C. At the end of this one year period the potency of this hetastarch plus histidine, toxin formulation is determined, using the mouse administration assay, to be essentially unchanged (i.e. potency differs by less than 5% from the original potency).

Example 10

Botulinum Toxin Pharmaceutical Composition Containing Arginine

Formulation IIE

100 U botulinum toxin type A purified neurotoxin complex pharmaceutical formulations are prepared in the same manner set forth in Example 1 above, except that the 0.5 milligrams of albumin was replaced by 600 µg of hetastarch. In addition 1 mg of arginine is added to the formulation. A lyophilized, hetastarch plus arginine, albumin-free, 100 U botulinum toxin type A complex, pharmaceutical composition is then stored for one year at −5° C. At the end of this one year period the potency of this hetastarch plus arginine, toxin formulation is determined, using the mouse administration assay, to be essentially unchanged (i.e. potency differs by less than 5% from the original potency).

Example 11

Botulinum Toxin Pharmaceutical Composition Containing an Amino Acid

Botulinum toxin type A purified neurotoxin complex pharmaceutical formulations can be prepared in the same manner set forth in Example 1 above, except that the 0.5 milligrams of albumin can be replaced by about 1 mg of an amino acid such as lysine, glycine, histidine or arginine. Thus a lyophilized, polysaccharide free, albumin free, glycine containing, botulinum toxin type A complex, pharmaceutical composition can be prepared and stored for at least one year $-5°$ C., and at the end of this period can have a potency of which is essentially unchanged (i.e. potency can differ by less than 5% from the original potency).

Example 12

Use of a Botulinum Toxin Pharmaceutical Composition

A 48 year old male is diagnosed with a spastic muscle condition, such as cervical dystonia. Between about $10^{-3}$ U/kg and about 35 U/kg of a botulinum toxin type A pharmaceutical composition containing 600 µg of hetastarch and 1 mg of an amino acid, such as lysine, is injected intramuscularly into the patient. Within 1-7 days the symptoms of the spastic muscle condition are alleviated and alleviation of the symptoms persists for at least from about 2 months to about 6 months.

Example 13

Reduced Antigenicity Botulinum Toxin Pharmaceutical Compositions Containing Hydroxyethyl Starch Upon Intramuscular Administration Formulations I and IIA An experiment can be carried out to evaluate the antigenicity of a botulinum toxin pharmaceutical composition containing 2-hydroxyethyl starch, with and without glycine, upon intramuscular administration.

Formulations I, II and IIA can be prepared as set forth by Example 1-3, respectively. The vacuum dried formulations can be removed from the freezer, reconstituted with sodium chloride and administered within four hours. Formulations I, II and IIA placebos can be prepared as previously set forth.

Six separate lots of rabbits can be given periodic intramuscular injections of Formulation I, Formulation II, Formulation IIA, or one of the three placebos (i.e. 3 control groups) over a six month period, at a high, but non-toxic dose level. It is expected that Formulations II and IIA will show a reduced generation of antibodies due to the reduced immunogenicity of the carbohydrate hydroxyethyl starch of Formulations II and IIA, as compared to the protein albumin present in Formulation I.

Example 14

Multiple Component Botulinum Toxin Formulations

As set forth briefly in the Definitions sections supra under the definition of "Pharmaceutical Composition" a multiple (i.e. two or more) component system for the making of a final formulation can provide the benefit of allowing incorporation of ingredients which are not sufficiently compatible for long-term shelf storage with the first component of the two component system or which for other reasons it is not desirable to include with the first component of the pharmaceutical composition. In this manner what I refer to as adaptive neurotoxin (i.e. botulinum toxin) formulations can be prepared.

rHSA and HSA can require secondary stabilizers such as N-Acetyltryptophan, sodium caprylate, fatty acids, surfactants and divalent cations for optimum long-term stability. Studies utilizing probe formulations indicate that some of these secondary stabilizers may induce enhanced potency or stability on neurotoxin (i.e. botulinum toxin) formulations. This example sets forth a way to add the appropriate concentration of these ingredients to obtain the desired effect. One way to accomplish this is to include the ingredient in the base formulation. Another is to add it to a base formulation prior to use. As set forth herein, Zinc, for example, may enhance the potency or liquid stability when added to an existing neurotoxin (i.e. botulinum toxin) formulation not containing zinc. Other beneficial stabilizing ingredients can likewise be added in this manner.

A limitation of the current Botox® formulation is related to the useful length of the product. Currently the recommended (for sterility reasons) life after reconstitution of Botox® is about four hours. This is due to the fact that the product contains no preservative. The diluent, saline, also contains no preservative. Studies indicate that incorporation of some preservatives can degrade the toxin over a long storage time (i.e. up to 2 years) of the vacuum dried product. However, utilization of a diluent containing a preservative would expose the toxin to degradation processes for a much shorter time while still providing preservative efficacy, that is the time of use, and thereby allow incorporation of a preservative.

A problem related to removal of protein stabilizers is clinical performance. Studies with hetastarch stabilized formulations indicate differences in performance (safety profile) possibly related to diffusion characteristics of the HES when compared to HSA. Other stabilizers (such as povidone) which perform similarly to HSA have thus far proven incompatible during storage, thereby limiting their usefulness. Incorporating them into a diluent or reconstitution vehicle would eliminate long-term exposure of the toxin to the incompatible species during which such degradation could occur. Therefore a HES or saline vacuum-dried formulation could be reconstituted in a vehicle containing a carrier, such as povidone, providing a shelf-stable product with the desired clinical performance.

Buffer salts or physiological pH conditions also may cause degradation during long-term storage. Enhanced storage stability may only be achievable by providing a suitable pH environment not suitable for injection (burning/stinging), such as low pH. A two-part system would overcome these limitations. A low pH shelf-stable formulation could be diluted or reconstituted using a buffer to overwhelm the capacity of the first composition, thereby providing a comfortable physiologic pH for injection.

Other advantages allow for changing the vehicle depending on use; i.e., the carrier could be selected according to the desired clinical diffusion characteristics. For example, toxin vacuum-dried in SWI, reconstituted with HES for one indication (cosmetic) and HSA for another (therapeutic). Stabilizing the toxin in SWFI, then reconstituting with saline (to obtain isotonicity) is another formulation option.

The final formulation might also be adapted to provide for patients allergic to a particular ingredient (a collagen vehicle substituted for a patient allergic to gelatin, for example). Otherwise, the base toxin formulation could be reconstituted with different albumins derived from a particular species for use in veterinary applications (equine serum albumin for use in horses, bovine serum albumin for use in cattle, as examples).

The basis of the invention is a formulation combined with adaptive, specialized vehicles/diluents to obtain the desired characteristics. The product can consist of three (or more) components; e.g., a vial containing a stable solid toxin and two pre-filled syringes containing differently formulated reconstitution vehicles.

Examples of Three-component Systems:

Version I (Solid/liquid):
    4. Toxin vacuum dried in NaCl
    5. Reconstitution vehicle containing HSA or rHA
    6. Second reconstitution vehicle containing HES In this version of a pharmaceutical composition wherein the active ingredient is a botulinum toxin, reconstitution can be carried out so as to obtain a formulation wherein the diffusion profile of the pharmaceutical composition upon intramuscular injection is the same as or different from diffusion profile of a pharmaceutical composition wherein the active ingredient is a botulinum toxin, but which contains albumin instead of HES.

Version II (Solid/liquid):
    4. Toxin vacuum dried in NaCl
    5. Reconstitution vehicle containing Povidone
    6. Second reconstitution vehicle containing HES In this version of a pharmaceutical composition (as in each of the additional versions set forth below) wherein the active ingredient is a botulinum toxin, reconstitution can be carried out so as to obtain a formulation wherein the diffusion profile of the pharmaceutical composition upon intramuscular injection is the same as or different from diffusion profile of a pharmaceutical composition wherein the active ingredient is a botulinum toxin, but which contains albumin instead of HES and povidone.

Version III (Solid/liquid):
    4. Toxin vacuum dried in SWFI (sterile water for injection)
    5. Reconstitution vehicle containing Povidone
    6. Second reconstitution vehicle containing HES (reconstitute with Povidone to obtain BOTOX® safety profile/HES to obtain modulated safety profile)

Version IV (Liquid/liquid):
    4. Toxin liquid stabilized with a buffer at pH 4
    5. Diluent liquid buffered to pH 7 containing HSA
    6. Second diluent liquid buffered to pH 7 containing HES (dilute with HSA diluent to obtain BOTOX® safety profile/HES to obtain modulated safety profile)

Version VI (Solid/liquid):
    4. Toxin vacuum dried in SWFI (sterile water for injection)
    5. Reconstitution vehicle containing HSA or rHA and preservative
    6. Second reconstitution vehicle containing HES and preservative (reconstitute with HSA/rHA to obtain BOTOX® safety profile/HES to obtain modulated safety profile; preservative is compatible with toxin to retain potency during specified time of use (e.g., 48 hours))

A pharmaceutical composition according to the invention disclosed herein has many advantages, including the following:

1. the pharmaceutical composition can be prepared free of any blood product, such as albumin and therefore free of any blood product infectious element such as a prion.

2. the pharmaceutical composition has stability and high % recovery of toxin potency comparable to or superior to that achieved with currently available pharmaceutical compositions.

3. reduced toxicity, as assessed by either intramuscular or intravenous administration.

4. reduced antigenicity.

Various publications, patents and/or references have been cited herein, the contents of which, in their entireties, are incorporated herein by reference.

Although the present invention has been described in detail with regard to certain preferred methods, other embodiments, versions, and modifications within the scope of the present invention are possible. For example, a wide variety of stabilizing polysaccharides and amino acids are within the scope of the present invention.

Accordingly, the spirit and scope of the following claims should not be limited to the descriptions of the preferred embodiments set forth above.

I claim:

1. A method for reducing a skin wrinkle in a patient, the method comprising the step of administering to a dermal region of said patient which has said skin wrinkle, a therapeutically effective amount of a pharmaceutical composition comprising polysaccharides, albumin and a botulinum toxin, wherein the pharmaceutical composition comprises a first polysaccharide and a second polysaccharide, wherein the first polysaccharide has a molecular weight of from about 20,000 Daltons (D) to about 50,000 Daltons, and the second polysaccharide has a molecular weight of from about 500,000 Daltons to about 1,000,000 Daltons.

2. A method for reducing a skin wrinkle in a patient, the method comprising the step of administering to a dermal region of said patient which has said skin wrinkle, a therapeutically effective amount of a pharmaceutical composition comprising a first polysaccharide and a second polysaccharide, albumin and a botulinum toxin, wherein the first polysaccharide has a molecular weight of from about 20,000 Daltons (D) to about 50,000 Daltons, and the second polysaccharide has a molecular weight of from about 500,000 Daltons to about 1,000,000 Daltons and wherein the first polysaccharide comprises a disaccharide.

3. A method for reducing a skin wrinkle in a patient, the method comprising the step of administering to a dermal region of said patient which has said skin wrinkle, a therapeutically effective amount of a pharmaceutical composition comprising a polysaccharide, albumin and a botulinum toxin, wherein the average molecular weight of a disaccharide unit of the polysaccharide is between about 345 D and about 1,000 D.

4. A method for reducing a skin wrinkle in a patient, the method comprising the step of administering to a dermal region of said patient which has said skin wrinkle, a therapeutically effective amount of a pharmaceutical composition comprising a polysaccharide, albumin and a botulinum toxin, wherein the polysaccharide is an ethyl ether substituted polysaccharide.

5. A method for reducing a skin wrinkle in a patient, the method comprising the step of administering to a dermal region of said patient which has said skin wrinkle, a therapeutically effective amount of a pharmaceutical composition comprising a polysaccharide, albumin and a botulinum toxin, wherein the polysaccharide comprises a plurality of linked glucopyranose units, each glucopyranose unit having a plurality of hydroxyl groups, wherein an average of about 6 to about 9 of the hydroxyl groups present on each 10 of the glucopyranoses present in the polysaccharide are substituted, through an ether linkage, with a compound of the formula $(CH_2)_n$-OH, where n can be an integer from 1 to 4.

6. The method of claim 5 wherein the skin wrinkle comprises a glabellar line.

7. The method of claim 5 wherein the composition further comprises a collagen.

8. The method of claim 5, wherein the botulinum toxin is botulinum toxin type A.

9. The method of claim 1, wherein the skin wrinkle comprises a glabellar line.

10. The method of claim 1, wherein the composition further comprises a collagen.

11. The method of claim 4 wherein the skin wrinkle comprises a glabellar line.

12. The method of claim 4 wherein the composition further comprises a collagen.

13. The method of claim 1 wherein the botulinum toxin is botulinum toxin type A.

14. The method of claim 4 wherein the botulinum toxin is botulinum toxin type A.

15. The method of claim 1, wherein the composition further comprises an amino acid.

16. The method of claim 3, wherein the composition further comprises an amino acid.

17. The method of claim 4, wherein the composition further comprises an amino acid.

18. The method of claim 5, wherein the composition further comprises an amino acid.

* * * * *

UNITED STATES PATENT AND TRADEMARK OFFICE
CERTIFICATE OF CORRECTION

PATENT NO. : 7,758,873 B2  Page 1 of 3
APPLICATION NO. : 11/303000
DATED : July 20, 2010
INVENTOR(S) : Terrence J. Hunt It is certified that error appears in the above-identified patent and that said Letters Patent is hereby corrected as shown below:

Title Page, Item (56) on page 2, in column 1, under "Other Publications", line 2, delete "Opthalmology" and insert -- Ophthalmology --, therefor.

Title Page, Item (56) on page 2, in column 1, under "Other Publications", line 20, delete "pruitus" and insert -- pruritus --, therefor.

Title Page, Item (56) on page 2, in column 1, under "Other Publications", line 30, delete "pruitus" and insert -- pruritus --, therefor.

Title Page, Item (56) on page 2, in column 1, under "Other Publications", line 39, delete "Actiation" and insert -- Activation --, therefor.

Title Page, Item (56) on page 2, in column 2, under "Other Publications", line 3, delete "C.," and insert -- C., et al., --, therefor.

Title Page, Item (56) on page 2, in column 2, under "Other Publications", line 17, delete "Notfallmd" and insert -- Notfallmed --, therefor.

Title Page, Item (56) on page 2, in column 2, under "Other Publications", line 28, delete "Nauyn" and insert -- Naunyn --, therefor.

Title Page, Item (56) on page 3, in column 1, under "Other Publications", line 36, delete "Laryngocope," and insert -- Laryngoscope, --, therefor.

Title Page, Item (56) on page 3, in column 2, under "Other Publications", line 8, delete "Transmisible" and insert -- Transmissible --, therefor.

In column 1, line 20, after "wrinkle" insert -- . --.

In column 3, line 48, after "type A" delete "is".

Signed and Sealed this

Fourteenth Day of September, 2010

David J. Kappos
*Director of the United States Patent and Trademark Office*

CERTIFICATE OF CORRECTION (continued)
U.S. Pat. No. 7,758,873 B2

In column 6, line 45, delete "haemagglutinin" and insert -- hemagglutinin --, therefor.

In column 7, line 45, delete "sublimus:" and insert -- sublimis: --, therefor.

In column 12, line 38, delete "Lippincoft," and insert -- Lippincott, --, therefor.

In column 14, line 67, after "polymers" insert -- . --.

In column 16, line 24, delete "free" and insert -- free" --, therefor.

In column 26, line 55, after "13-9" insert -- . --.

In column 30, line 47, delete "morbundity," and insert -- moribundity, --, therefor.

In column 30, line 58, delete "piloerrection," and insert -- piloerection, --, therefor.

In column 30, line 59, delete "morbundity)" and insert -- moribundity) --, therefor.

In column 31, line 40-41, delete "chromorrhinorrhea" and insert -- chromorhinorrhea --, therefor.

In column 32, line 24, delete "morbundity," and insert -- moribundity, --, therefor.

In column 37, line 8, delete "4." and insert -- 1. --, therefor.

In column 37, line 9, delete "5." and insert -- 2. --, therefor.

In column 37, line 10, delete "6." and insert -- 3. --, therefor.

In column 37, line 22, delete "4." and insert -- 1. --, therefor.

In column 37, line 23, delete "5." and insert -- 2. --, therefor.

In column 37, line 24, delete "6." and insert -- 3. --, therefor.

In column 37, line 36, delete "4." and insert -- 1. --, therefor.

In column 37, line 37, delete "5." and insert -- 2. --, therefor.

In column 37, line 38, delete "6." and insert -- 3. --, therefor.

In column 37, line 44, delete "4." and insert -- 1. --, therefor.

In column 37, line 45, delete "5." and insert -- 2. --, therefor.

In column 37, line 46, delete "6." and insert -- 3. --, therefor.

In column 37, line 52, delete "4." and insert -- 1. --, therefor.

In column 37, line 53, delete "5." and insert -- 2. --, therefor.

In column 37, line 55, delete "6." and insert -- 3. --, therefor.